(12) United States Patent
Suwara et al.

(10) Patent No.: US 11,111,523 B2
(45) Date of Patent: Sep. 7, 2021

(54) NUCLEIC ACID PROBE WITH SINGLE FLUOROPHORE LABEL BOUND TO INTERNAL CYTOSINE FOR USE IN LOOP MEDIATED ISOTHERMAL AMPLIFICATION

(71) Applicant: Mast Group Limited, Liverpool (GB)

(72) Inventors: Monika Iwona Suwara, Waterloo (GB); Sajid Javed, Macclesfield (GB); Elizabeth Ann Gillies, Bolton (GB)

(73) Assignee: MAST GROUP LIMITED, Liverpool (GB)

( * ) Notice: Subject to any disclaimer, the term of this patent is extended or adjusted under 35 U.S.C. 154(b) by 0 days.

(21) Appl. No.: 16/245,190

(22) Filed: Jan. 10, 2019

(65) Prior Publication Data

US 2019/0127785 A1 May 2, 2019

Related U.S. Application Data

(63) Continuation of application No. 15/032,011, filed as application No. PCT/GB2014/053238 on Oct. 30, 2014, now abandoned.

(30) Foreign Application Priority Data

Oct. 30, 2013 (GB) .................................. 1319180

(51) Int. Cl.
  *C12Q 1/68* (2018.01)
  *C12Q 1/6825* (2018.01)
  (Continued)

(52) U.S. Cl.
  CPC .......... *C12Q 1/6825* (2013.01); *C12Q 1/689* (2013.01); *C12Q 1/6816* (2013.01);
  (Continued)

(58) Field of Classification Search
  CPC ........................................................ C12Q 1/68
  (Continued)

(56) References Cited

U.S. PATENT DOCUMENTS

2002/0106653 A1* 8/2002 Kurane ............... C12Q 1/6818
  435/6.12
2005/0260581 A1 11/2005 Fontana et al.
  (Continued)

FOREIGN PATENT DOCUMENTS

CN 102 703 433 A 10/2012
EP 0 515 194 A2 11/1992
  (Continued)

OTHER PUBLICATIONS

Ishiguro et al. (Fluorescence Detection of Specific Sequence of Nucleic Acids by Oxazole Yellow-Linked Oligonucleotides. Homogeneous Quantitative Monitoring of In Vitro Transcription, Nucleic Acids Research, vol. 24, Issue 24, Dec. 1, 1996, pp. 4992-4997).*
  (Continued)

*Primary Examiner* — Aaron A Priest
(74) *Attorney, Agent, or Firm* — Knobbe, Martens, Olson & Bear, LLP

(57) ABSTRACT

The disclosure relates to novel probes for use in LAMP detection methods. The probes contain a single fluorophore label bound to an internal cytosine residue of the probe. The probes are particularly useful in the detection of chlamydia and gonorrhea infections in a patient.

12 Claims, 30 Drawing Sheets

Specification includes a Sequence Listing.

Schematic of MAST DNA probe

5' T GCA CT GCGAA TC TG CAG 3'

(51) Int. Cl.
*C12Q 1/6816* (2018.01)
*C12Q 1/6844* (2018.01)
*C12Q 1/689* (2018.01)

(52) U.S. Cl.
CPC ..... *C12Q 1/6844* (2013.01); *C12Q 2531/101* (2013.01); *C12Q 2531/119* (2013.01); *C12Q 2563/107* (2013.01); *C12Q 2565/107* (2013.01); *C12Q 2600/16* (2013.01)

(58) Field of Classification Search
USPC ........................................................ 435/6.1
See application file for complete search history.

(56) References Cited

U.S. PATENT DOCUMENTS

| | | | |
|---|---|---|---|
| 2006/0088866 A1 | 4/2006 | Cottrell | |
| 2006/0246447 A1 | 11/2006 | Inose et al. | |
| 2007/0238125 A1 | 10/2007 | Uematsu et al. | |
| 2008/0311579 A1 | 12/2008 | French et al. | |
| 2010/0233715 A1* | 9/2010 | Yonekawa | C12Q 1/6851 435/6.1 |
| 2011/0244460 A1* | 10/2011 | Hirai | C12Q 1/6848 435/6.11 |
| 2012/0088244 A1* | 4/2012 | Owen | C12Q 1/703 435/6.12 |
| 2012/0107817 A1* | 5/2012 | Iguchi | C12Q 1/6886 435/6.11 |
| 2013/0143212 A1* | 6/2013 | Hosomi | C12Q 2527/143 435/6.11 |
| 2014/0349295 A1* | 11/2014 | Hosaka | C12N 15/1034 435/6.11 |
| 2015/0203894 A1* | 7/2015 | Yotoriyama | G01N 27/447 204/543 |

FOREIGN PATENT DOCUMENTS

| | | |
|---|---|---|
| EP | 2 218 780 A1 | 8/2010 |
| EP | 2 570 492 A2 | 3/2013 |
| EP | 2 574 680 A1 | 4/2013 |
| EP | 2 653 560 A1 | 10/2013 |
| JP | 2014-093996 A | 5/2014 |
| WO | WO 00/79009 A1 | 12/2000 |
| WO | WO 02/14555 A1 | 2/2002 |
| WO | WO 2005/098036 A1 | 10/2005 |
| WO | WO 2007/010268 A2 | 1/2007 |

OTHER PUBLICATIONS

Hwang, Single-Labeled Oligonucleotides Showing Fluorescence Changes Upon Hybridization with Target Nucleic Acids, Molecules, Jan. 8, 2018;23(1):124. doi: 10.3390/molecules23010124.*

French, et al. 2008 "Hybeacon' probes for rapid DNA sequence detection and allele discrimination" *Moleulcar Humana Press*: 171-185.

Ikeda, et al. 2009 "Doubly thiazole orange-labeled cytidine for functional expansion of a hybridization-sensitive probe" *Tetrahedron Letters* 50: 7191-7195.

Ishiguru et al. 1996 "Flurorescence detection of specific sequence of nucleic acids by oxazole yellow-linked oligonucleotides. Homogeneous quantitative monitoring of in vitro transcription" *Nucleic Acids Research* 24(24): 4992-4997.

Matteucci; and Caruthers 1980 "Synthesis of Deoxyoligonucleotides on a polymer support" *J. Am. Chem. Soc.*, 103(11): 3185-3191.

Mayer et al. 2004 "1-Ethynylpyrene as a tunable and versatile molecular beacon for DNA" *ChemBioChem* 5: 865-868.

Tong & Mallinson 2002 "Moving to nucleic acid-based detection of genital Chlamydia trachomatis" *Expert Rev. Mol. Diagn.* 2(3): 257-266.

Utekal, et al. 2015 "Real-time PCR-based genotyping from whole blood using Taq DNA polymerase and a buffer supplemented with 1,2-propanediol and trehalose" *Journal of Immunological Methods* 415: 178-182.

Yamane 2000 "Smart probe: A novel fluorescence quenching-based oligonucleotide probe carrying a fluorophore and an intercalator" *Nucleic Acids Symposium Series No. 44*: 297-298.

* cited by examiner

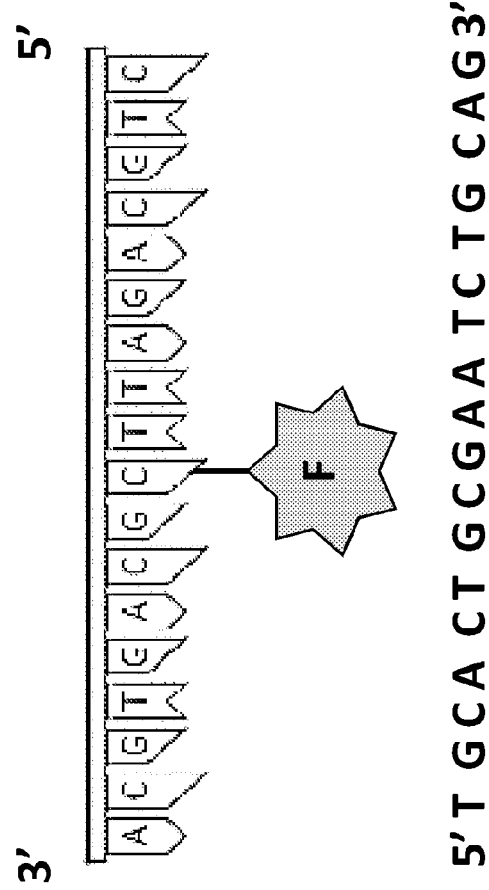

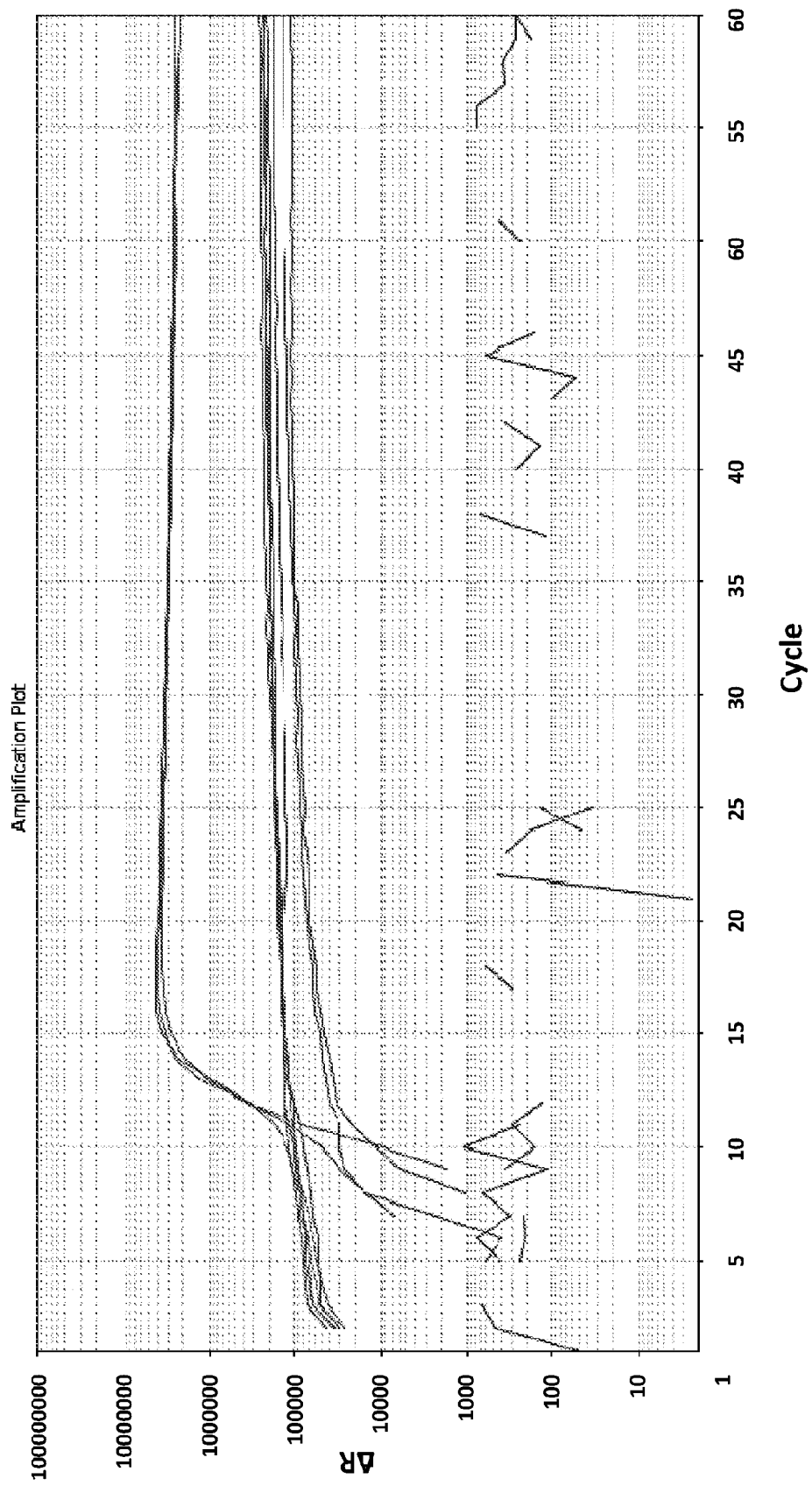

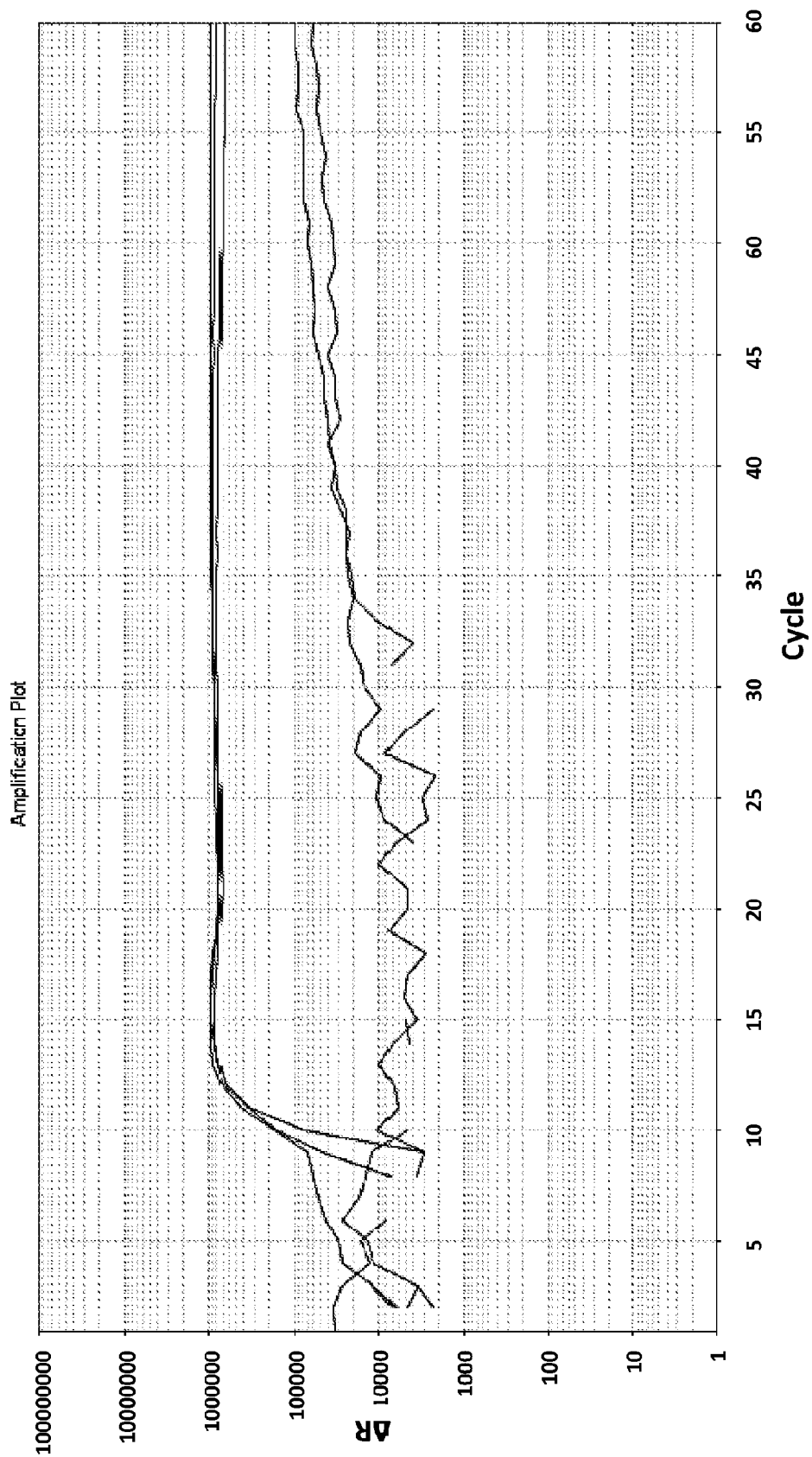

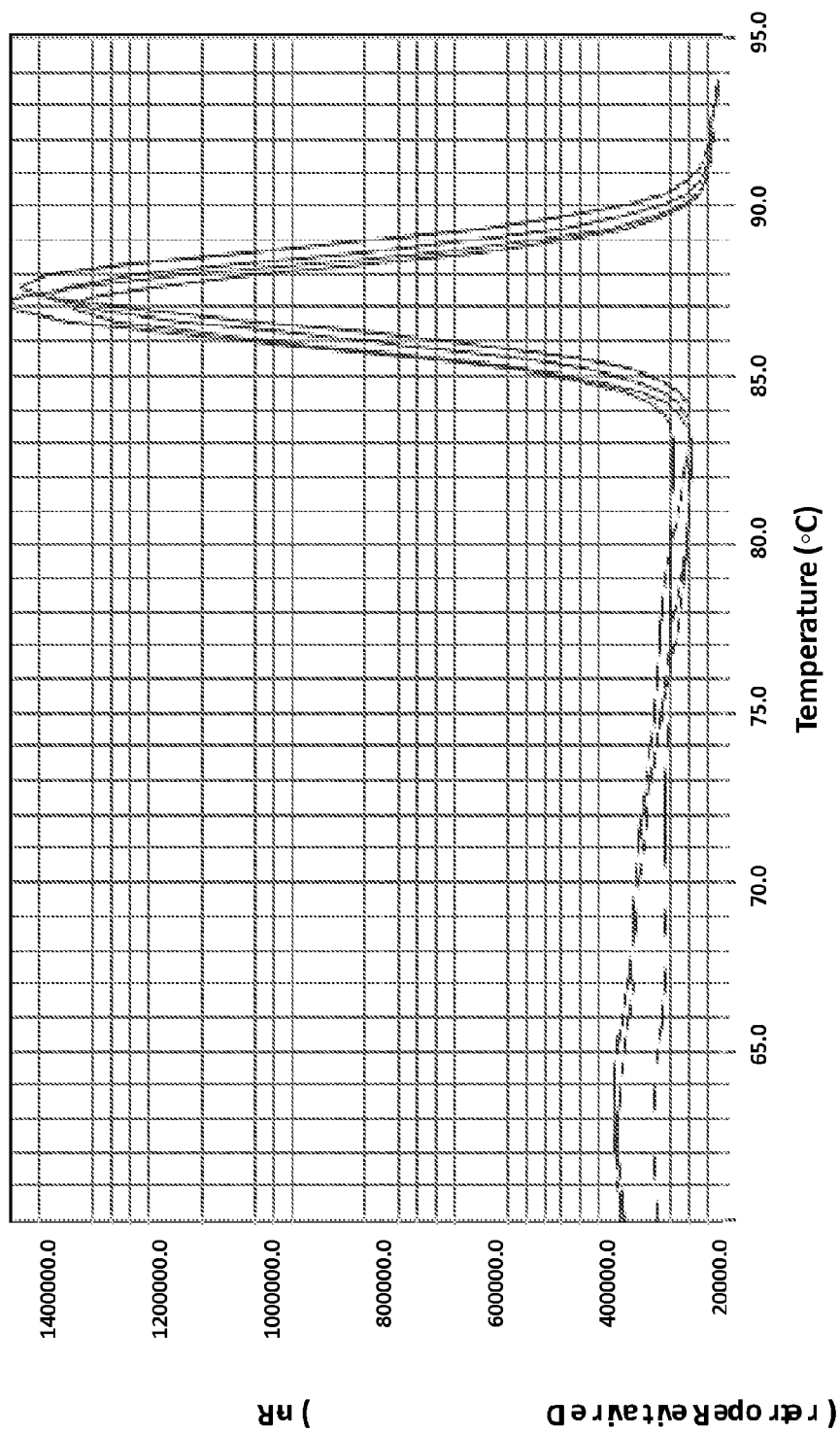

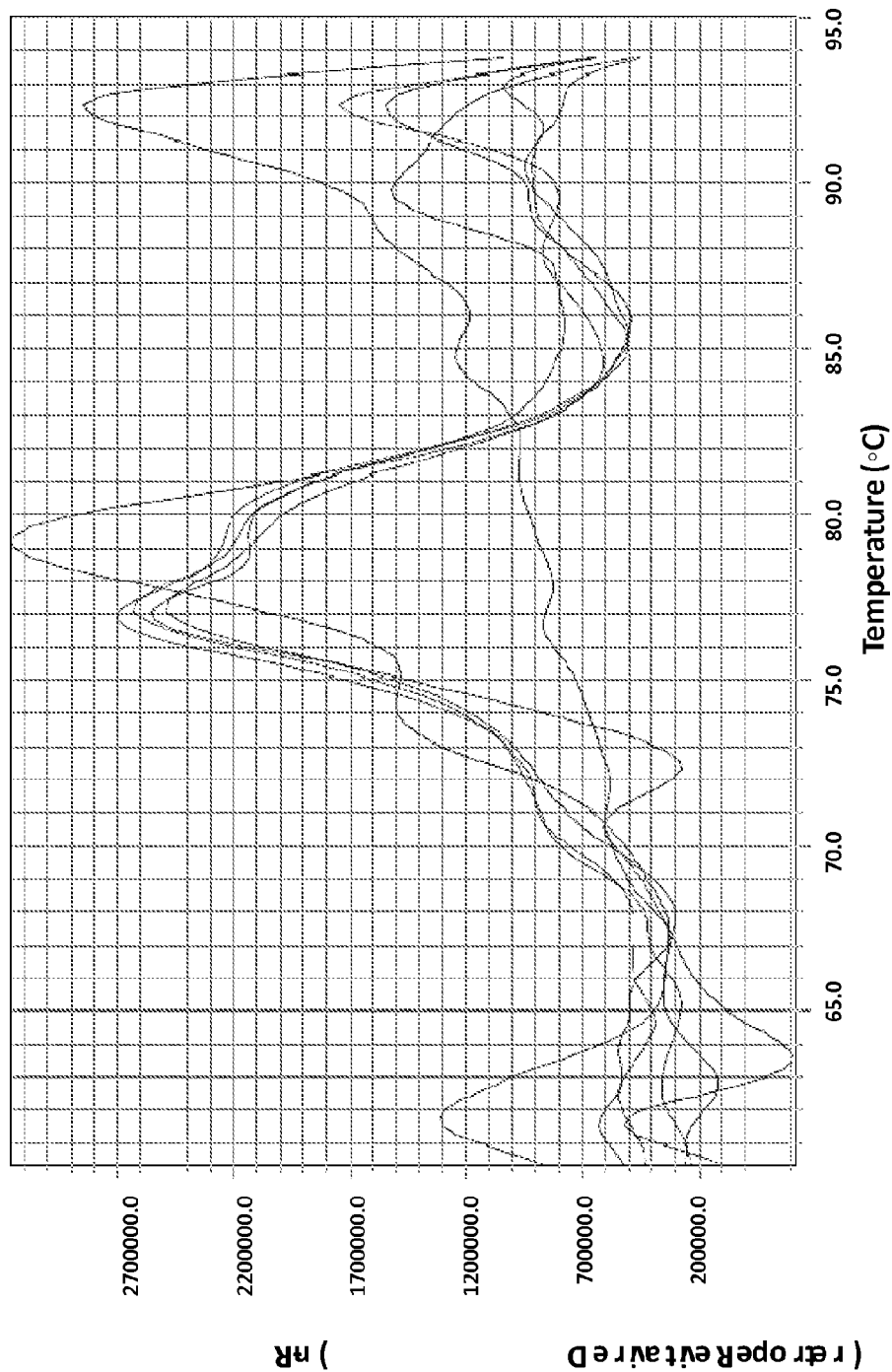

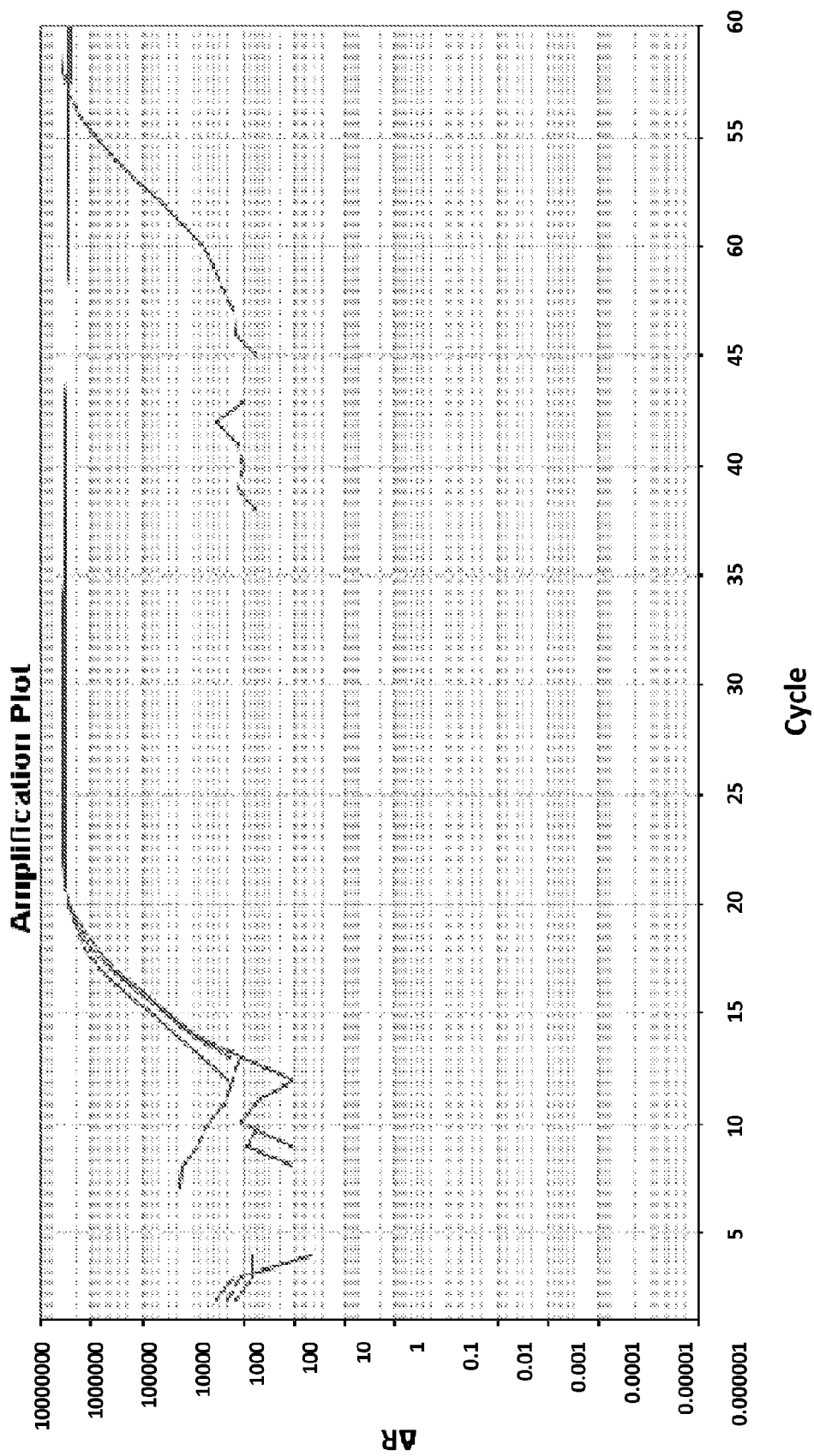

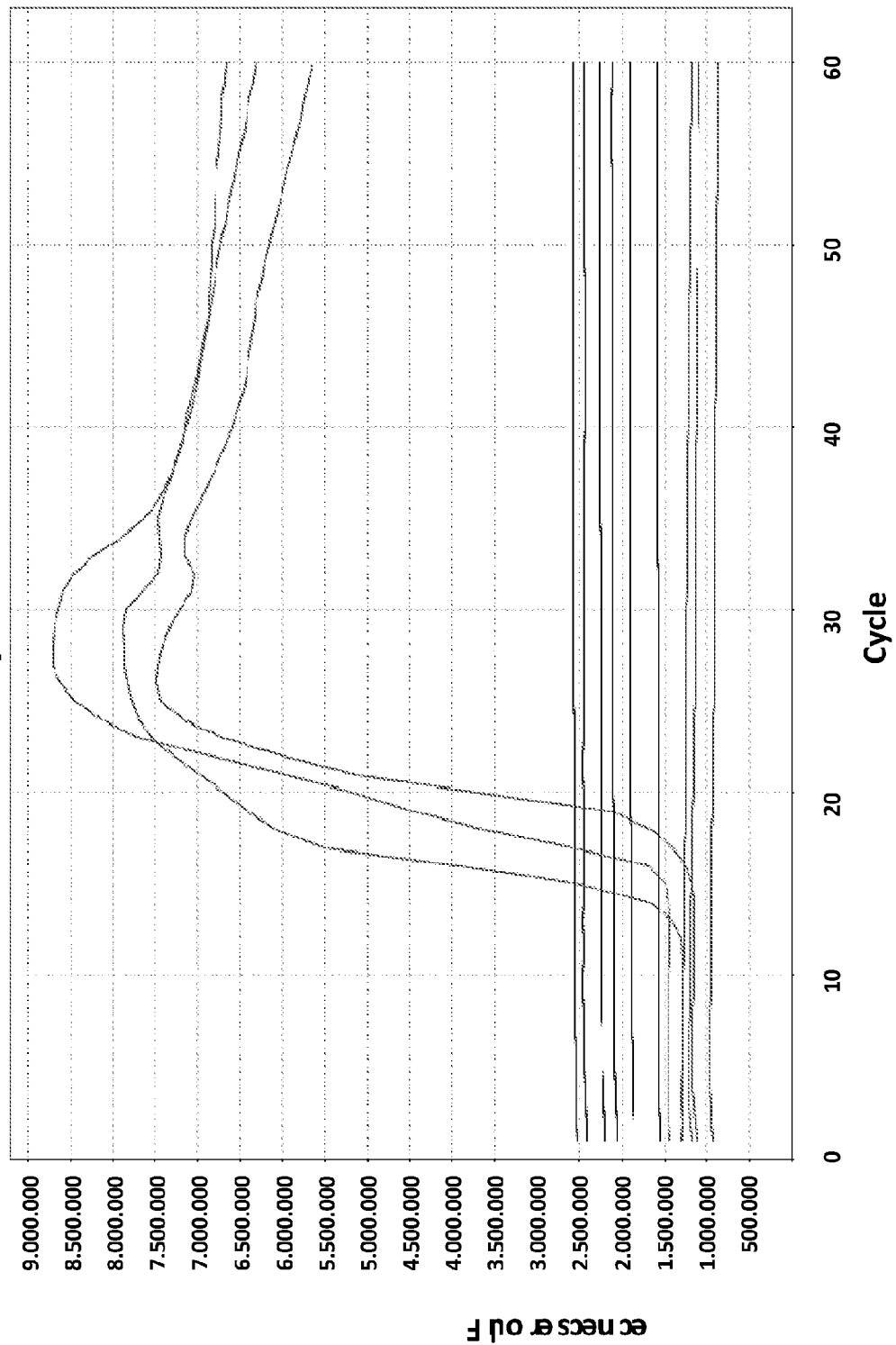

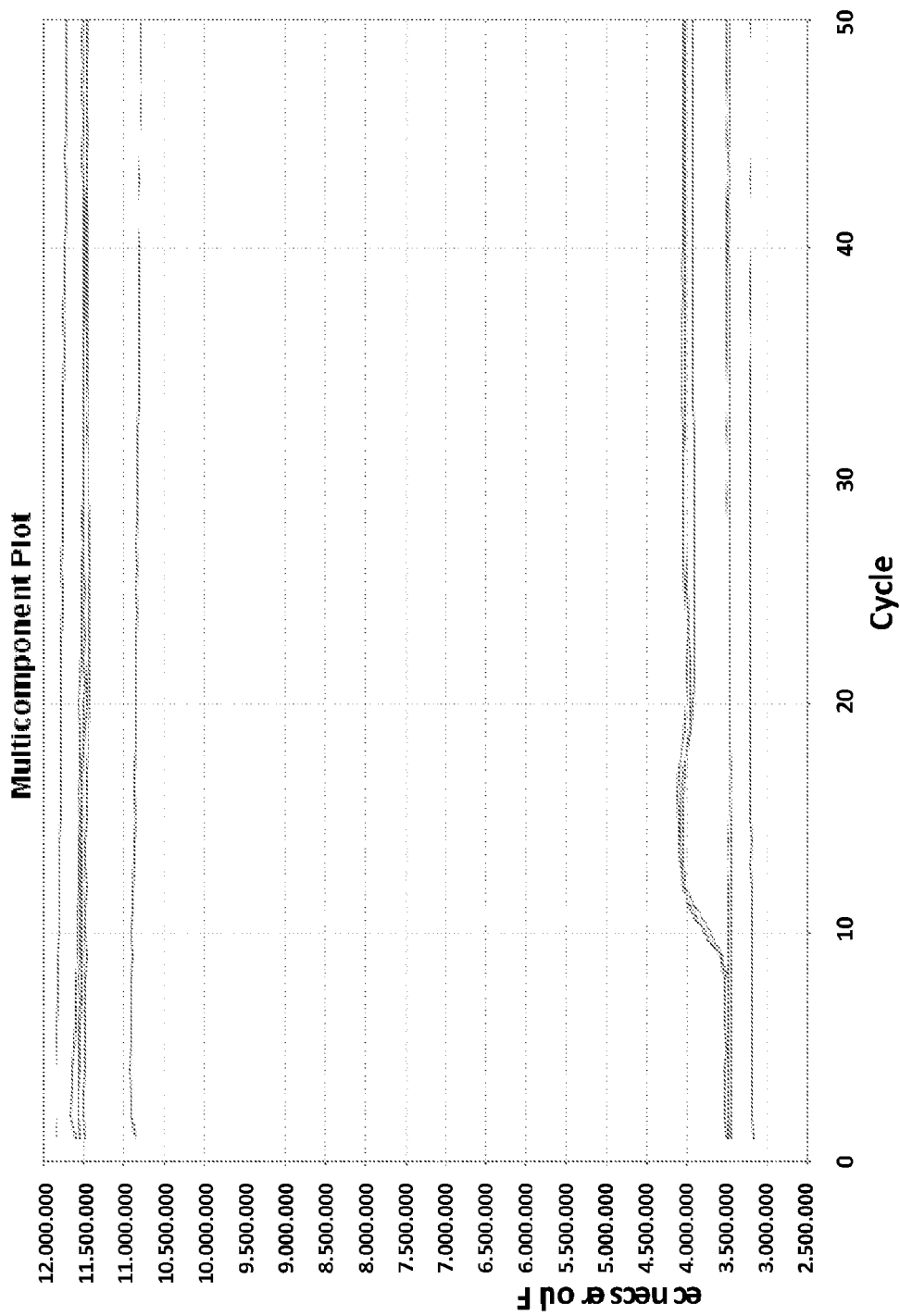

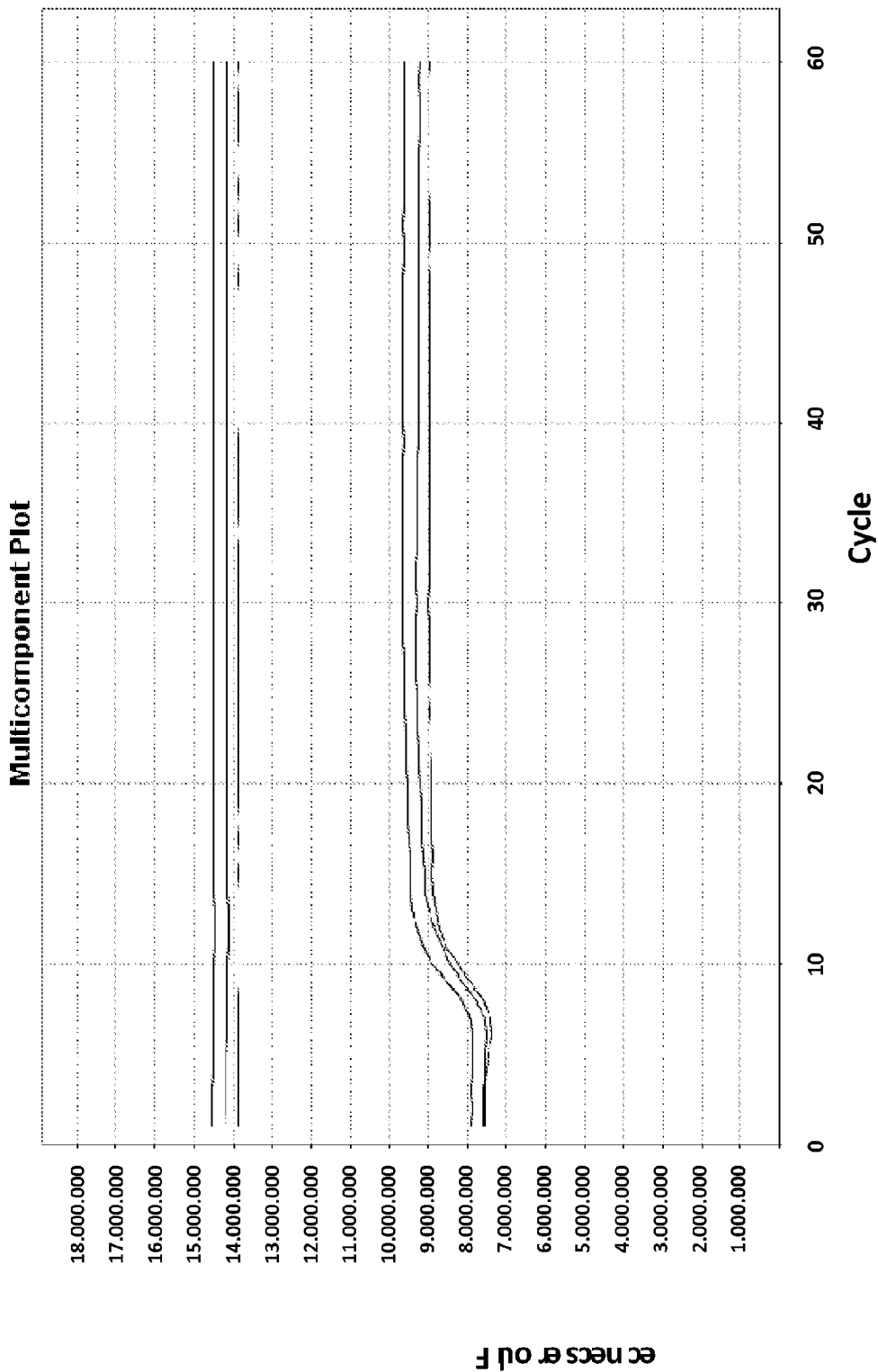

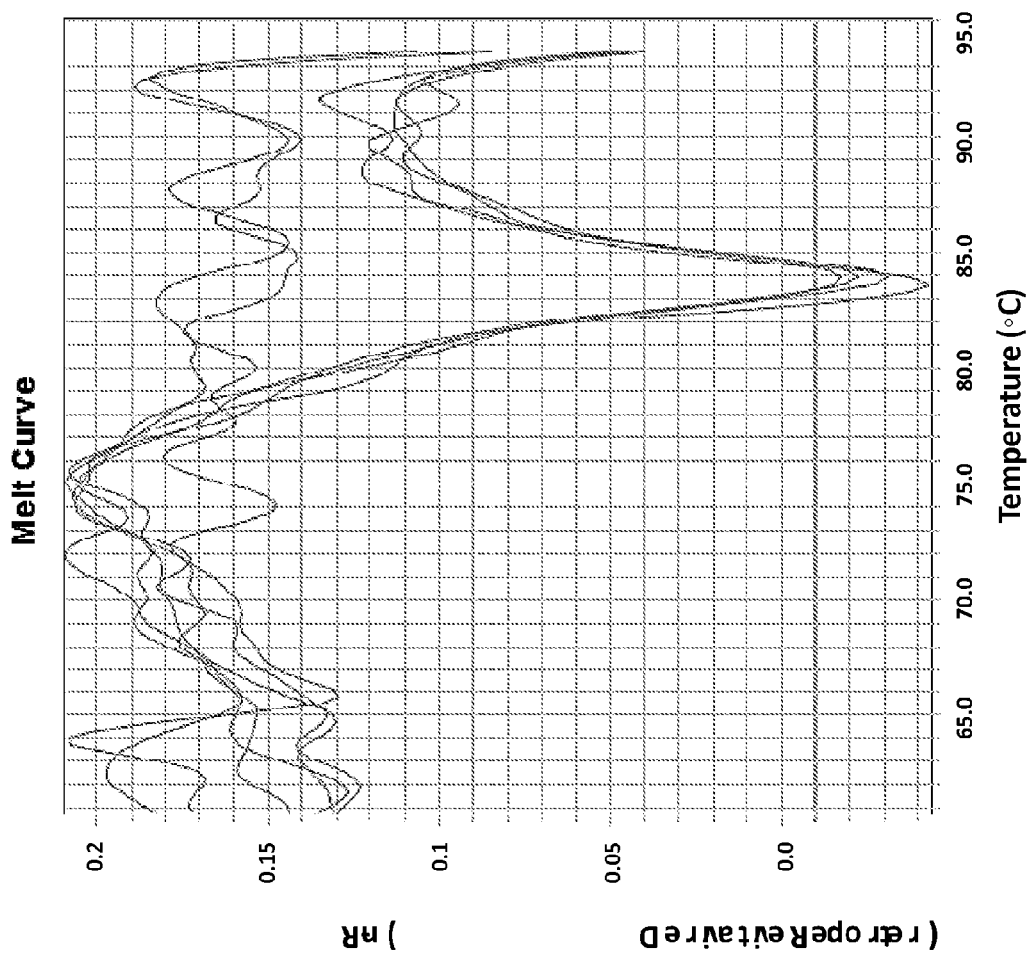

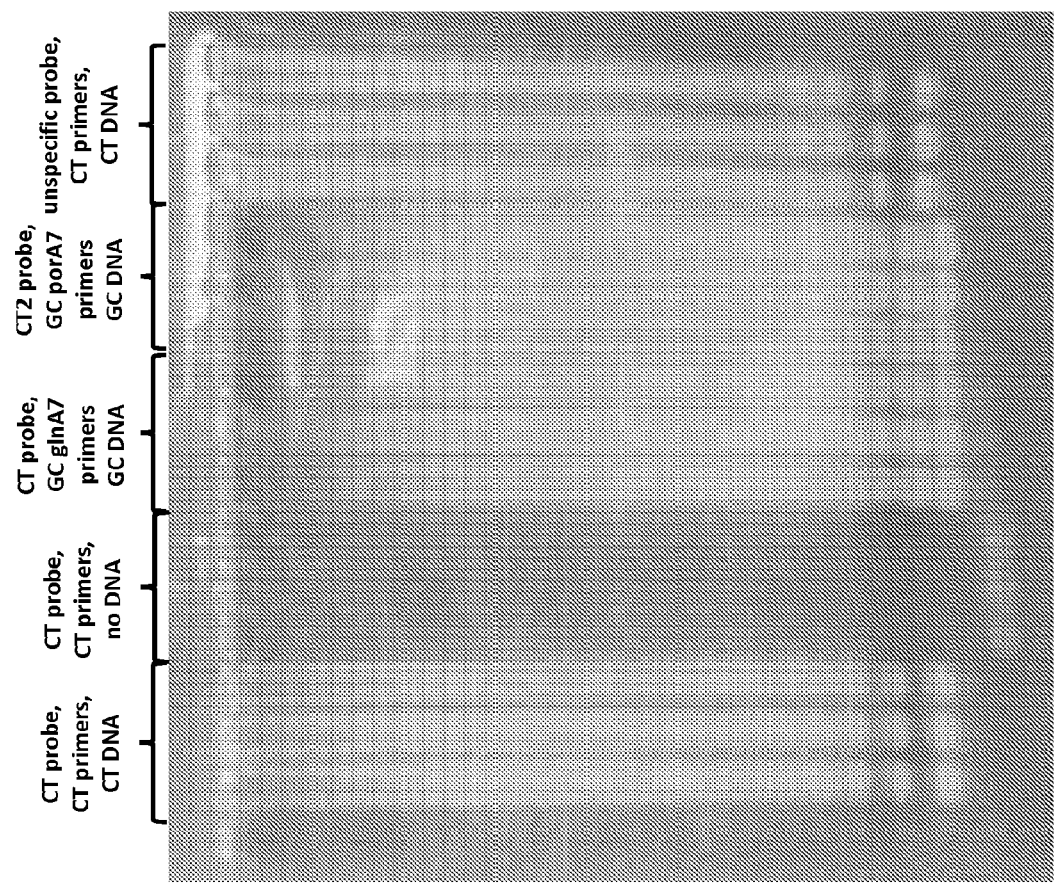

SEQUENCE LISTING

```
<160> NUMBER OF SEQ ID NOS: 26

<210> SEQ ID NO 1
<211> LENGTH: 19
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (9)..(9)
<223> OTHER INFORMATION: cytosine labeled with FAM
```

-continued

<400> SEQUENCE: 1
gtgcacgccc caatagaat                                                19

<210> SEQ ID NO 2
<211> LENGTH: 19
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (10)..(10)
<223> OTHER INFORMATION: cytosine labeled with FAM

<400> SEQUENCE: 2
taagataacc ccgcacgtg                                                19

<210> SEQ ID NO 3
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (9)..(9)
<223> OTHER INFORMATION: cytosine labeled with FAM

<400> SEQUENCE: 3
tcgagcaacc gctgtgac                                                 18

<210> SEQ ID NO 4
<211> LENGTH: 23
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (10)..(10)
<223> OTHER INFORMATION: cytosine labeled with ALEXA546

<400> SEQUENCE: 4
gcgaacatac cagctatgat caa                                           23

<210> SEQ ID NO 5
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (8)..(8)
<223> OTHER INFORMATION: cytosine labeled with JOE

<400> SEQUENCE: 5
atgttcacca tggcggag                                                 18

<210> SEQ ID NO 6
<211> LENGTH: 23
<212> TYPE: DNA
<213> ORGANISM: Artificial Sequence
<220> FEATURE:
<223> OTHER INFORMATION: probe
<220> FEATURE:
<221> NAME/KEY: modified_base
<222> LOCATION: (23)..(23)

<223> OTHER INFORMATION: cytosine labeled with FAM

<400> SEQUENCE: 6

| ccagggtatc taatcctgtt tgc | 23 |
|---|---|

<210> SEQ ID NO 7
<211> LENGTH: 7471
<212> TYPE: DNA
<213> ORGANISM: Chlamydia trachomatis

<400> SEQUENCE: 7

| tttgcaactc ttggtggtag actttgcaac tcttggtggt agactttgca actcttggtg | 60 |
|---|---|
| gtagacttgg tcataatgga cttttgttaa aaaatttctt aaaatcttag agctccgatt | 120 |
| ttgaatagct ttggttaaga aaatgggctc gatggctttc cataaaagta gattgttctt | 180 |
| aacttttggg gacgcgtcgg aaatttggtt atctacttta tctcatctaa ctagaaaaaa | 240 |
| ttatgcgtct gggattaact ttcttgtttc tttagagatt ctggatttat cggaaacctt | 300 |
| gataaaggct atttctcttg accacagcga atctttgttt aaaatcaagt ctctagatgt | 360 |
| ttttaatgga aaagtcgttt cagaggcctc taaacaggct agagcggcat gctacatatc | 420 |
| tttcacaaag tttttgtata gattgaccaa gggatatatt aaacccgcta ttccattgaa | 480 |
| agattttgga aacactacat tttttaaaat ccgagacaaa atcaaaacag aatcgatttc | 540 |
| taagcaggaa tggacagttt ttttgaagc gctccggata tgaattata gagactattt | 600 |
| aatcggtaaa ttgattgtac aagggatccg taagttagac gaaattttgt ctttgcgcac | 660 |
| agacgatcta ttttttgcat ccaatcagat ttcctttcgc attaaaaaaa gacagaataa | 720 |
| agaaaccaaa attctaatca catttcctat cagcttaatg gaagagttgc aaaaatacac | 780 |
| ttgtgggaga atgggagag tatttgtttc taaaataggg attcctgtaa caacaagtca | 840 |
| ggttgcgcat aattttaggc ttgcagagtt ccatagtgct atgaaaataa aaattactcc | 900 |
| cagagtactt cgtgcaagcg ctttgattca tttaaagcaa ataggattaa aagatgagga | 960 |
| aatcatgcgt atttcctgtc tctcatcgag acaaagtgtg tgttcttatt gttctgggga | 1020 |
| agaggtaagt cctctagtac aaacacccac aatattgtga tataattaaa attatattca | 1080 |
| tattctgttg ccagaaaaaa cacctttagg ctatattaga gccatcttct ttgaagcgtt | 1140 |
| gtcttctcga gaggatttat cgtacgcaaa tatcatcttt gcggttgcgt gtcccgtgac | 1200 |
| cttcattatg tcggagtctg agcaccctag gcgtttgtac tccgtcacag cggttgctcg | 1260 |
| aagcacgtgc ggggttatct aaaagggat tgcagcttgt agtcctgctt gagagaacgt | 1320 |
| gcgggcgatt tgccttaacc ccaccatttt tccggagcga gttacgaaga caaaacctct | 1380 |
| tcgttgaccg atgtactctt gtagaaagtg cataaacttc tgaggataag ttataataat | 1440 |
| cctcttttct gtctgacggt tcttaagctg ggagaaagaa atggtagctt gttggaaaca | 1500 |
| aatctgacta atctccaagc ttaagacttc agaggagcgt ttacctcctt ggagcattgt | 1560 |
| ctgggcgatc aaccaatccc gggcgttgat ttttttagc tcttttagga aggatgctgt | 1620 |
| ttgcaaactg ttcatcgcat ccgttttttac tatttccctg gttttaaaaa atgttcgact | 1680 |
| attttcttgt ttagaaggtt gcgctatagc gactattcct tgagtcatcc tgtttaggaa | 1740 |
| tcttgttaag gaaatatagc ttgctgctcg aacttgttta gtaccttcgg tccaagaagt | 1800 |
| cttggcagag gaactttttt taatcgcatc taggattaga ttatgattta aagggaaaa | 1860 |
| ctcttgcaga ttcatatcca aagacaatag accaatcttt tctaaagaca aaaaagatcc | 1920 |
| tcgatatgat ctacaagtat gtttgttgag tgatgcggtc caatgcataa taacttcgaa | 1980 |

```
taaggagaag cttttcatgc gtttccaata ggattcttgg cgaattttta aaacttcctg    2040
ataagacttt tcgctatatt ctaacgacat ttcttgctgc aaagataaaa tccctttacc    2100
catgaaatcc ctcgtgatat aacctatccg caaaatgtcc tgattagtga aataatcagg    2160
ttgttaacag gatagcacgc tcggtatttt tttatataaa catgaaaact cgttccgaaa    2220
tagaaaatcg catgcaagat atcgagtatg cgttgttagg taaagctctg atatttgaag    2280
actctactga gtatattctg aggcagcttg ctaattatga gtttaagtgt tcccatcata    2340
aaaacatatt catagtattt aaatacttaa aagacaatgg attacctata actgtagact    2400
cggcttggga agagcttttg cggcgtcgta tcaaagatat ggacaaatcg tatctcgggt    2460
taatgttgca tgatgcttta tcaaatgaca agcttagatc cgtttctcat acggttttcc    2520
tcgatgattt gagcgtgtgt agcgctgaag aaaatttgag caatttcatt ttccgctcgt    2580
ttaatgagta caatgaaaat ccattgcgta gatctccgtt tctattgctt gagcgtataa    2640
agggaaggct tgatagtgct atagcaaaga cttttctat tcgcagcgct agaggccggt     2700
ctatttatga tatattctca cagtcagaaa ttggagtgct ggctcgtata aaaaaagac     2760 gagcagcgtt ctctgagaat caaaattctt tctttgatgg cttcccaaca ggatacaagg    2820
atattgatga taaaggagtt atcttagcta aaggtaattt cgtgattata gcagctaggc    2880
catctatagg gaaaacagct ttagctatag acatggcgat aaatcttgcg ttactcaac    2940 agcgtagagt tggtttccta tctctagaaa tgagcgcagg tcaaattgtt gagcggattg    3000
ttgctaattt aacaggaata tctggtgaaa aattacaaag agggggatctc tctaaagaag   3060 aattattccg agtggaagaa gctggagaaa cagttagaga atcacatttt tatatctgca   3120
gtgatagtca gtataagctt aatttaatcg cgaatcagat ccggttgctg agaaaagaag   3180
atcgagtaga cgtaatatt atcgattact tgcagttgat caactcatcg gttggagaaa    3240
atcgtcaaaa tgaaatagca gatatatcta gaaccttaag aggtttagcc tcagagctaa   3300
acattcctat agtttgttta tcccaactat ctagaaaagt tgaggataga gcaaataaag   3360
ttcccatgct ttcagatttg cgagacagcg gtcaaataga gcaagacgca gatgtgattt   3420
tgtttatcaa taggaaggaa tcgtcttcta attgtgagat aactgttggg aaaaatagac    3480
atggatcggt tttctcttcg gtattacatt tcgatccaaa aattagtaaa ttctccgcta   3540
ttaaaaaagt atggtaaatt atagtaactg ccacttcatc aaaagtccta tccaccttga   3600
aaatcagaag tttggaagaa gacctggtca atctattaag atatctccca aattggctca   3660
aaatgggatg gtagaagtta taggtcttga ttttctttca tctcattacc atgcattagc   3720
agctatccaa agattactga ccgcaacgaa ttacaagggg aacacaaaag gggttgtttt    3780
atccagagaa tcaaatagtt ttcaatttga aggatggata ccaagaatcc gttttacaaa   3840
aactgaattc ttagaggctt atggagttaa gcggtataaa acatccagaa ataagtatga   3900
gtttagtgga aaagaagctg aaactgcttt agaagccttg taccatttag acatcaacc    3960 gttttaata gtggcaacta gaactcgatg gactaatgga acacaaatag tagaccgtta   4020
ccaaactctt tctccgatca ttaggattta cgaaggatgg gaaggtttaa ctgacgaaga   4080
aaatatagat atagacttaa cacctttaa ttcaccatct acacggaaac ataaaggatt    4140
cgttgtagag ccatgtccta tcttggtaga tcaaatagaa tcctactttg taatcaagcc   4200
tgcaaatgta taccaagaaa taaaaatgcg tttcccaaac gcatcaaagt atgcttacac   4260
atttatcgac tgggtgatta cagcagctgc gaaaaagaga cgaaaattaa ctaaggataa   4320
```

```
ttcttggcca gaaaacttgt tattaaacgt taacgttaaa agtcttgcat atattttaag    4380
gatgaatcgg tacatctgta caaggaactg gaaaaaaatc gagttagcta tcgataaatg    4440
tatagaaatc gccattcagc ttggctggtt atctagaaga aaacgcattg aatttctgga    4500
ttcttctaaa ctctctaaaa aagaaattct atatctaaat aaagagcgct ttgaagaaat    4560
aactaagaaa tctaaagaac aaatggaaca agaatctatt aattaatagc aggcttgaaa    4620
ctaaaaacct aatttattta aagctcaaaa taaaaaagag ttttaaaatg ggaaattctg    4680
gtttttattt gtataacact gaaaactgcg tctttgctga taatatcaaa gttgggcaaa    4740
tgacagagcc gctcaaggac cagcaaataa tccttgggac aaaatcaaca cctgtcgcag    4800
ccaaaatgac agcttctgat ggaatatctt taacagtctc caataattca tcaaccaatg    4860
cttctattac aattggtttg gatgcggaaa agcttaccag gcttattcta gaaaagttgg    4920
gaaatcaaat tcttgatgga attgctgata ctattgttga tagtacagtc caagatattt    4980
tagacaaaat cacaacagac ccttctctag gtttgttgaa agcttttaac aactttccaa    5040
tcactaataa aattcaatgc aacgggtat tcactcccag taacattgaa actttattag     5100
gaggaactga aataggaaaa ttcacagtca cacccaaaag ctctgggagc atgttcttag    5160
tctcagcaga tattattgca tcaagaatgg aaggcggcgt tgttctagct ttggtacgag    5220
aaggtgattc taagccctgc gcgattagtt atggatactc atcaggcgtt cctaatttat    5280
gtagtctaag aaccagcatt actaatacag gattgactcc aacaacgtat tcattacgtg    5340
taggcggttt agaaagcggt gtggtatggg ttaatgccct ttctaatggc aatgatattt    5400
taggaataac aaatacttct aatgtatctt ttttggaagt aatacctcaa acaaacgctt    5460
aaacaatttt tattggattt ttcttatagg ttttatattt agagaaaaca gttcgaatta    5520
cggggttgt tatgcaaaat aaaagaaaag tgagggacga ttttattaaa attgttaaag    5580
atgtgaaaaa agatttcccc gaattagacc taaaaatacg agtaaacaag gaaaaagtaa    5640
ctttcttaaa ttctcccctta gaactctacc ataaaagtgt ctcactaatt ctaggactgc    5700
ttcaacaaat agaaaactct ttaggattat cccagactc tcctgttctt gaaaaattag     5760
aggataacag tttaaagcta aaaaaggctt tgattatgct tatcttgtct agaaaagaca    5820
tgttttccaa ggctgaatag acaacttact ctaacgttgg agttgatttg cacaccttag    5880
tttttttgctc ttttaaggga ggaactggaa aaacaacact ttctctaaac gtgggatgca   5940
acttggccca atttttaggg aaaaaagtgt tacttgctga cctagacccg caatccaatt    6000
tatcttctgg attgggggct agtgtcagaa ataaccaaaa aggcttgcac gacatagtat    6060
acaaatcaaa cgatttaaaa tcaatcattt gcgaaacaaa aaaagatagt gtggacctaa    6120
ttcctgcatc attttatcc gaacagttta gagaattgga tattcataga ggacctagta    6180
acaacttaaa gttatttctg aatgagtact gcgctccttt ttatgacatc tgcataatag    6240
acactccacc tagcctagga gggttaacga aagaagcttt tgttgcagga gacaaattaa    6300
ttgcttgttt aactccagaa cctttttcta ttctagggtt acaaaagata cgtgaattct    6360
taagttcggt cggaaaacct gaagaagaac acattcttgg aatagctttg tctttttggg    6420
atgatcgtaa ctcgactaac caaatgtata tagacattat cgagtctatt tacaaaaaca    6480
agcttttttc aacaaaaatt cgtcgagata tttctctcag ccgttctctt cttaaagaag    6540
attctgtagc taatgtctat ccaaattcta gggccgcaga agatattctg aagttaacgc    6600
atgaaatagc aaatatttg catatcgaat atgaacgaga ttactctcag aggacaacgt    6660
gaacaaacta aaaaaagaag cggatgtctt ttttaaaaaa aatcaaactg ccgcttctct    6720
```

```
agattttaag aagacacttc cttccattga actattctca gcaactttga attctgagga    6780
aagtcagagt ttggatcgat tatttttatc agagtcccaa aactattcgg atgaagaatt    6840
ttatcaagaa gacatcctag cggtaaaact gcttactggt cagataaaat ccatacagaa    6900
gcaacacgta cttcttttag gagaaaaaat ctataatgct agaaaaatcc tgagtaagga    6960
tcacttctcc tcaacaactt tttcatcttg gatagagtta gttttagaa ctaagtcttc     7020 tgcttacaat gctcttgcat attacgagct ttttataaac ctccccaacc aaactctaca    7080
aaaagagttt caatcgatcc cctataaatc cgcatatatt ttggccgcta gaaaaggcga    7140
tttaaaaacc aaggtcgatg tgataggaa agtatgtgga atgtcgaact catcggcgat     7200
aagggtgttg gatcaatttc ttccttcatc tagaaacaaa gacgttagag aaacgataga    7260
taagtctgat ttagagaaga atcgccaatt atctgatttc ttaatagaga tacttcgcat    7320
catatgttcc ggagtttctt tgtcctccta taacgaaaat cttctacaac agcttttga    7380 actttttaag caaagagct gatcctccgt cagctcatat atatatttat tatatatata    7440
tttatttagg gatttgattt tacgagagag a                                   7471

<210> SEQ ID NO 8
<211> LENGTH: 743
<212> TYPE: DNA
<213> ORGANISM: Neisseria gonorrhoeae

<400> SEQUENCE: 8
gccggcggcg cgcgacccg ttggggcaat agggaatcct ttgtcggctt ggcaggcgaa      60
ttcggcacgc tgcgcgccgg ccgcgttgcg aatcagtttg acgatgccag ccaagccatt    120
gatccttggg acagcaacaa tgatgtggct tcgcaattgg gtattttcaa acgccacgac    180
gatatgccgg tttccgtacg ctacgactcc ccggactttt ccggtttcag cggcagcgtc    240
caattcgttc cggctcaaaa cagcaagtcc gcctatacgc cggctcattg gactactgtg    300
tataacacta acggtactac tactactttc gttccggctg ttgtcggcaa gcccggatcg    360
gatgtgtatt atgccggtct gaattacaaa aatggcggtt ttgccgggaa ctatgccttt    420
aaatatgcga gacacgccaa tgtcggacgt aatgcttttg agttgttctt gctcggcagt    480
gggagtgatg aagccaaagg taccgatccc ttgaaaaacc atcaggtaca ccgcctgacg    540
ggcggctatg gggaaggcgg cttgaatctc gccttggcgg ctcagttgga tttgtctgaa    600
aatgccgaca aaaccaaaaa cagtacgacc gaaattgccg ccactgcttc ctaccgcttc    660
ggtaatacag tcccgcgcat cagctatgcc catggtttcg actttgtcga acgcagtcag    720
aaacgcgaac ataccagcta tga                                            743

<210> SEQ ID NO 9
<211> LENGTH: 1356
<212> TYPE: DNA
<213> ORGANISM: Neisseria gonorrhoeae

<400> SEQUENCE: 9
cccgctttgt cgatttgcgc ttcaccgata ccaaaggcaa gcagcaccac tttaccgtgc     60
ctgcgcgcat cgtgttggaa gaccccgaag agtggtttga aaacggaccg gcgtttgacg    120
gctcgtccat cggcggctgg aaaggcattg aggcttccga tatgcagctg cgtcccgatg    180
cgtccacagc cttcgtcgat cctttttatg atgatgttac cgtcgtcatt acctgcgacg    240
tcatcgaccc tgccgacggt cagggttacg accgcgaccc gcgctccatc gcacgccgcg    300
```

```
ccgaagccta tttgaaatct tccggtatcg gcgacaccgc ctatttcggc cccgaacccg    360
aattcttcgt cttcgacggc gtagaatttg aaaccgacat gcacaaaacc cgttacgaaa    420
tcacgtccga aagcggcgcg tgggcaagcg gcctgcatat ggacggtcaa acaccggcc     480 accgccccgc cgtcaaaggc ggctacgcgc ccgtcgcgcc gattgactgc ggtcaagatt    540
tgcgctccgc catggtgaac attttggaag gactcggcat cgaagtcgaa gtccaccaca    600
gcgaagtcgg taccgcagc caaatggaaa tcggcacccg tttcgccact ttggtcaaac     660
gcgccgacca aacccaagat atgaaatacg tcatccaaaa cgttgcccac aatttcggca    720
aaaccgccac ctttatgccc aaaccgatta tgggcgacaa cggcagcggt atgcacgtcc    780
accaatccat ttggaaagac ggtcaaaacc tgttcgcagg cgacggctat gccggtttgt    840
ccgataccgc gctctactac atcggcggca tcatcaaaca cgccaaagcc ctgaacgcga    900
ttaccaatcc gtccaccaac tcctacaaac gcctcgtgcc gcactttgaa gcaccgacca    960
aattggccta ttccgccaaa aaccgttccg cttccatccg tatcccgtct gtgaacagca   1020
gcaaggcgcg ccgcatcgaa gcgcgttttc ccgacccgac cgccaacccg tatttggcat   1080
ttgccgccct gctgatggcc ggtttggacg gcattcaaaa caaaatccat ccgggcgacc   1140
ctgccgataa aaacctgtac gacctgccgc cggaagaaga cgcgctcgtc ccgaccgtct   1200
gcgcttcttt ggaagaagca cttgccgccc tcaaggtcga ccacgaattc ctgctgcgcg   1260
gcggcgtgtt cagcaaagac tggatcgaca gctacatcgc cttttaaagag gaagatgtcc   1320 gccgcatccg tatggcgccg cacccgctgg aatttg                             1356
```

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tctacaagag tacatcggtc a                                                21

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
tgaagcgttg tcttctcg                                                    18

<210> SEQ ID NO 12
<211> LENGTH: 39
<212> TYPE: DNA
<213> ORGANISM: Artificial Sequence
<220> FEATURE:
<223> OTHER INFORMATION: primer

<400> SEQUENCE: 12
gcagcttgta gtcctgcttg agtcttcgta actcgctcc                             39

<210> SEQ ID NO 13
<211> LENGTH: 39
<212> TYPE: DNA
<213> ORGANISM: Artificial Sequence
<220> FEATURE:
<223> OTHER INFORMATION: primer

```
<400> SEQUENCE: 13
tcgagcaacc gctgtgaccc ttcattatgt cggagtctg                               39

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
cgggcgattt gccttaac                                                     18

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
tacaaacgcc tagggtgc                                                     18

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
accaaaaaca gtacgaccga                                                   20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aagtgcgctt ggaaaaatcg                                                   20

<210> SEQ ID NO 18
<211> LENGTH: 38
<212> TYPE: DNA
<213> ORGANISM: Artificial Sequence
<220> FEATURE:
<223> OTHER INFORMATION: primer

<400> SEQUENCE: 18
atgggcatag ctgatgcgcg aattgccgcc actgcttc                               38

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
tcgactttgt cgaacgcagt caaatcgaca ccggcgatga                             40

<210> SEQ ID NO 20
```

```
<211> LENGTH: 23
<212> TYPE: DNA
<213> ORGANISM: Artificial Sequence
<220> FEATURE:
<223> OTHER INFORMATION: primer

<400> SEQUENCE: 20
gcgaacatac cagctatgat caa                                              23

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tcatatcttg ggtttggtcg                                                  20

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
ctgcatatgg acggtcaaa                                                   19

<210> SEQ ID NO 23
<211> LENGTH: 37
<212> TYPE: DNA
<213> ORGANISM: Artificial Sequence
<220> FEATURE:
<223> OTHER INFORMATION: primer

<400> SEQUENCE: 23
cgaagtccac cacagcgaat ttgaccaaag tggcgaa                               37

<210> SEQ ID NO 24
<211> LENGTH: 39
<212> TYPE: DNA
<213> ORGANISM: Artificial Sequence
<220> FEATURE:
<223> OTHER INFORMATION: primer

<400> SEQUENCE: 24
cttcgatgcc gagtccttcc gattgactgc ggtcaagat                             39

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
caaatggaaa tcggcaccc                                                   19

<210> SEQ ID NO 26
<211> LENGTH: 18
<212> TYPE: DNA
<213> ORGANISM: Artificial Sequence
```

-continued

```
<220> FEATURE:
<223> OTHER INFORMATION: primer

<400> SEQUENCE: 26
atgttcacca tggcggag                                                    18
```

NUCLEIC ACID PROBE WITH SINGLE FLUOROPHORE LABEL BOUND TO INTERNAL CYTOSINE FOR USE IN LOOP MEDIATED ISOTHERMAL AMPLIFICATION

FIELD OF THE INVENTION

The present invention relates to a probe for the detection of a nucleic acid, a method using said probe and a kit of parts. Preferably the probe of the invention is useful in a method for the detection of nucleic acids derived from *Chlamydia trachomatis* and/or *Neisseria gonorrhoeae* and may be used in the diagnosis of Chlamydia and/or Gonorrhoea infections.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 29736213_1.TXT, the date of creation of the ASCII text file is Jan. 10, 2019, and the size of the ASCII text file is 17.5 KB.

BACKGROUND OF THE INVENTION

Nucleic acid amplification is one of the most valuable tools in the life sciences field, including application-oriented fields such as clinical medicine, in which diagnosis of infectious diseases, genetic disorders and genetic traits is particularly benefited. In addition to the widely used PCR-based detection (Saiki R. K., Scharf, S., Faloona, F., Mullis, K. B., Horn, G. T., Erlich, H. A. and Arnheim, N. (1985) Science, 230, 1350-1354), several amplification methods have been invented. Examples include nucleic acid sequence-based amplification (NASBA), self-sustained sequence replication (3SR) and loop-mediated isothermal amplification (LAMP). PCR uses heat denaturation of double-stranded DNA products to promote the next round of DNA synthesis. 3SR and NASBA eliminate heat denaturation by using a set of transcription and reverse transcription reactions to amplify the target sequence.

These methods can amplify target nucleic acids to a similar magnitude, all with a detection limit of less than 10 copies and within an hour or so. They require either a precision instrument for amplification or an elaborate method for detection of the amplified products due to poor specificity of target sequence selection. Despite the simplicity and the obtainable magnitude of amplification, the requirement for a high precision thermal cycler in PCR prevents this powerful method from being widely used, such as in private clinics as a routine diagnostic tool. In contrast, LAMP is a method that can amplify a few copies of DNA to over 100 in less than an hour under isothermal conditions and with greater specificity.

As with other molecular-probe based technologies identified above, loop-mediated isothermal amplification (LAMP) assays can be used to detect the presence of specific microorganisms in a sample. However, the detection methods are based on direct visual detection, turbidity or via a non-specific DNA intercalating dye. Direct visual measurement is end point measurement and is unable to provide real time analysis. Turbidity and non-specific intercalating dyes do provide real time analysis of amplification which occurs however this is non-specific i.e. all amplification is detected whether this is true positive amplification or false amplification due to mis-priming, cross specificity.

SUMMARY OF THE INVENTION

In accordance with a first aspect of the present invention there is provided a probe for isothermal nucleic acid amplification comprising an oligonucleotide probe sequence complementary to a region of a target nucleic acid sequence, wherein said oligonucleotide probe sequence has only one fluorophore ligand and which ligand is bound to an internal cytosine base and wherein said oligonucleotide probe sequence does not have a 3' end terminator.

In a preferred embodiment to oligonucleotide probe sequence is a DNA sequence and the target nucleic acid sequence is a DNA sequence.

Preferably, fluorescence increases to indicate the presence of the target nucleic acid in a sample.

The cytosine base is preferably substantially centrally disposed along the oligonucleotide's length. There are particular benefits associated with labeling the probe internally at a cytosine base. The specificity of the DNA product amplified in an isothermal reaction may be confirmed using a melt curve analysis. However due to a large number of product variants generated in this reaction and a low resolution of melt curve analysis, using intercalating dyes like V13, it is very difficult to distinguish between specific and unspecific DNA products generated under isothermal conditions. Commonly used probes such as TaqMan® probe are not compatible with LAMP technology due to the strand displacement activity of BST polymerase. The probe of the invention is elongated and becomes incorporated into a DNA product during isothermal amplification, which allows for performing a melt curve analysis on the generated product. In the probe of the invention, the fluororphore is conjugated to an internal cytosine complementary to guanine in the antisense strand. Guanine affects the excitation state of many fluorophores resulting in a formation of unique melt curve signatures and allows distinguishing between specific and unspecific products generated under isothermal conditions.

The oligonucleotide does not contain a ddNTP at its 3' end which enables incorporation of the labelled oligonucleotide into the amplicon. Thus, the 3' end of the probe is not "blocked".

The fluorophore may comprise any one or more selected from the following: FAM, JOE, TET, HEX, TAMRA, ROX, ALEXA and ATTO.

The probe may comprise the following sequence:

5'XnC*Xm3'

Where n is >1, m is >3, X is nucleotide base; and * is a fluorophore. Preferably, the nucleotide base is selected from A, T, C and G. Preferably, n is more than 1 to 20 or less, more preferably more than 1 to 10 or less. Preferably, m is more than 3 to 20 or less, more preferably more than 3 to 10 or less. It is contemplated that all combinations of lengths of probe covered by the possible number of nucleotides that n or m make take by the preceding ranges are disclosed.

Preferably, the probe may comprise a sequence selected from any one of the following sequences:

(CT PB1-FAM internal)
SEQ ID NO. 2:
TAAGATAAC[C-FAM]CCGCACGTG

-continued (GC porA7-joe loopF)
SEQ ID NO. 4:
GCGAACATA[C-ALEXA546]CAGCTATGATCAA or (GC glnA7-ALEXA546 loopB)
SEQ ID NO. 5:
ATGTTCA[C-JOE]CATGGCGGAG.

The fluorescence is preferably increased when the oligonucleotide is incorporated into the target nucleic acid sequence which results in a change in the configuration of the amplicon-probe complex leading to an alteration of the fluorophore excitation state.

The cytosine bound to the fluorophore ligand is not disposed at or proximate to the 5' or 3' end. More preferably it is not disposed in the first 3 bases from either the 5' or 3' end. Preferably the cytosine bound to the fluorophore is disposed at the middle base of the probe.

In accordance with a further aspect of the present invention, there is provided an isothermal nucleic acid amplification probe as described hereinabove.

In accordance with a further aspect of the present invention, there is provided a loop-mediated isothermal amplification probe as described above.

Methods and compositions for determining at least one target nucleic acid in a mixture of nucleic acids generally employ a probe, a hybridizing reagent, and one or more phosphate bond-forming enzymes associated with any required nucleotide triphosphates to form a nucleic acid chain.

These methods usually involve amplification, such as including the use of a promoter in conjunction with a RNA polymerase, a restriction site where only one strand is cleaved and is then displaced by extension with a DNA polymerase, or a circular hybridizing reagent, where concatenated repeats are produced. Detection of the amplified nucleic acid may take many forms but preferably via a fluorophore.

In accordance with a further aspect of the present invention, there is provided a method of detecting a target nucleic acid in a sample comprising:
 a. amplifying a target nucleic acid in the sample to provide an amplified nucleic acid;
 b. probing the amplified nucleic acid with a probe as described hereinabove; and
 c. detecting the presence of a single or multiple target nucleic acids.

The target nucleic acid may be that from a micro-organism, fungi, yeast, virus, human, animal, plant etc. The target nucleic acid for LAMP is known to enable LAMP primers and appropriately specific probes to be synthesised. Thus, the presence or absence of said micro-organism, fungi, yeast, virus, human, animal or plant in a sample can be determined. Preferably the target nucleic acid is from *Chlamydia trachomatis* or *Neisseria gonorrhoeae*.

Preferably, fluorescence increases to indicate the presence of the target nucleic acid in a sample.

The process is isothermal, and allows for amplification in a single stage or sequential stages in a single vessel, where all of the reagents are compatible.

In a further aspect, the present invention provides a method of diagnosing Chlamydia and/or Gonorrhea in a patient, comprising
 providing a sample derived from the patient;
 adding one or more probes of the present invention to the sample; and
 detecting the presence of a nucleic acid derived from *Chlamydia trachomatis* and/or *Neisseria gonorrhoeae* wherein an increase in the fluorescence of the probe indicates the presence of a *Chlamydia trachomatis* and/or *Neisseria gonorrhoeae* infection.

The sample may be treated by routine methods to enable the probe to bind with any target nucleotide present in the sample. Such treatment may include centrifuging and lysing the sample to release any target nucleic from the infecting microorganism.

In one embodiment, a single type of probe specific for a nucleic acid from either *Chlamydia trachomatis* or *Neisseria gonorrhoeae* is used in the method such that either only *Chlamydia trachomatis* or only *Neisseria gonorrhoeae* is detected in the sample.

In a preferred embodiment, at least two different probes are added to the sample wherein a first probe is labelled with a first fluorescent label and is specific for probing *Chlamydia trachomatis* nucleic acid and a second probe is labelled with a different fluorescent label to the first probe and is specific for probing *Neisseria gonorrhoeae* nucleic acid. In this embodiment, it is possible to simultaneously detect a Chlamydia and a Gonorrhea infection in a single sample derived from a patient.

In one aspect of the method of the invention, the sample from the patient may be a blood sample, urine sample, serum sample or saliva sample.

In accordance with a further aspect of the present invention there is provided a kit comprising a probe as described hereinabove, LAMP reaction buffer containing a polymerase enzyme, dNTPS and LAMP primers for the target.

In one embodiment a positive and negative control may be included in the kit. The reagents may be presented as wet reagents or in lyophilised form.

The buffer used in the method or kit of the invention comprises dNTPs at a concentration of from 1-10 mM, one or more salts at a concentration of from 2-20 mM, Tris pH8.8 at a concentration of from 10-100 mM, Trehalose at a concentration of from 10-100 mM, BST polymerase at an amount of from 1U-12U and 0.01%-1% 1,2 propanediol.

BRIEF DESCRIPTION OF THE DRAWINGS

FIG. 1 is a schematic of DNA probe of the invention.

FIGS. 2A to 2F show amplification plots generated with the CT PB1 (FIG. 2A and FIG. 2D), GC glnA7 (FIG. 2B and FIG. 2E) and GC porA7 (FIG. 2C and FIG. 2F) primers in V6.21 buffer containing V13 (FIGS. 2A, 2B and 2C) or V6.21p buffer without V13 dye (FIGS. 2D, 2E and 2F).

FIGS. 6A to 6D show the results of a test to confirm the DNA product specificity with a probe of the invention in loop mediated isothermal amplification.

FIG. 7 shows amplification plots generated with CT PB1 primers in V6.21 buffer containing V13 or V6.21p buffer without V13 dye but in the presence of CT PB1 terminal probe (complementary to loop region) with an internal C conjugated with FAM and 3' terminator (3'ddC).

FIGS. 8A and 8B show the amplification plots generated in V6.21p buffer containing ROX in the presence of CT PB1 primers and CT PB1 terminal probe with an internal cytosine conjugated with FAM (FIG. 8A), and universal primers and 3'UP probe with 3' terminal cytosine conjugated with FAM (FIG. 8B).

FIGS. 9A to 9C show the amplification plots generated with CT PB1 primers in V6.21p buffer without V13 in the presence of CT PB1 internal probe with an internal C conjugated with FAM and a reference dye (ROX).

FIGS. 10A to 10C show the validation of CT PB1-FAM probe specificity. FIG. 10A shows amplification plots generated with CT PB1-FAM probe in the presence of CT DNA and CT primers.

DETAILED DESCRIPTION OF CERTAIN EMBODIMENTS OF THE INVENTION

Abbreviations

Figure 2A:
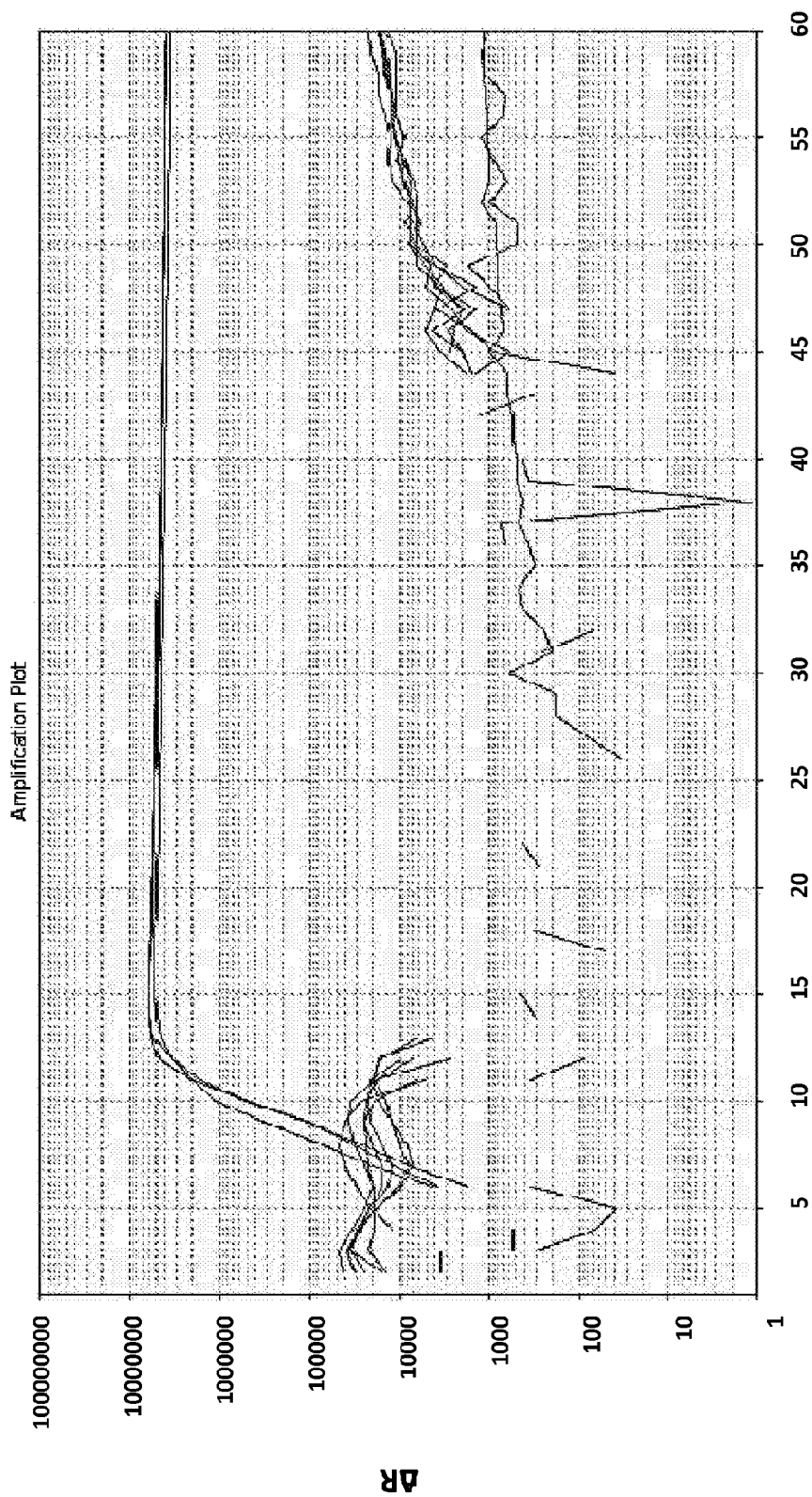

CT—*Chlamydia trachomatis*
GC—*Neisseria gonorrhoeae*
GlnA7—Glutamine synthetase
PorA7—porin protein A7
LAMP—loop mediated isothermal amplification
PCR—polymerase chain reaction.

The present invention will now be described, by way of example only, with reference to the following examples and figures.

LAMP Reaction

V13 based detection of the target CT and GT DNA by LAMP was performed using LAMP V6.21 reaction buffer developed by the Applicant. Probe based detection of the target DNA was performed in V6.21p (without V13). The LAMP primer concentrations were as follows: CT PB1—0.8 µM FIP & BIP primer, 0.2 µM F3 & B3 and 0.4 µM Loop primers, GC porA7 and GC glnA7—2 µM FIP & BIP primer, 0.25 µM F3 & B3 and 0.5 µM Loop primers. All probes were used at a final concentration of 0.625 µM. LAMP reactions were run for 60 mins at a constant temperature of 63 C using ABI7500 real-time PCR machine. Readouts of the fluorescent signal were obtained in Sybr-Green/FAM, Joe or Cy3 channel as appropriate.

```
Probe sequences
SEQ ID NO. 1:
GTGCACGC[C-FAM]CCAATAGAAT (CT PB1-FAM internal)
SEQ ID NO. 2:
TAAGATAAC[C-FAM]CCGCACGTG (CT PB1-FAM terminal)
SEQ ID NO. 3:
TCGAGCAA[C-FAM]CGCTGTGAC[ddC]

(GC porA7-joe loopF)
SEQ ID NO. 4:
GCGAACATA[C-ALEXA546]CAGCTATGATCAA (GC glnA7-ALEXA546 loopB)
SEQ ID NO. 5:
ATGTTCA[C-JOE]CATGGCGGAG
or

SEQ ID NO. 6:
CCA GGG TAT CTA ATC CTG TTT G[C-FAM].
```

Target Sequences

The target DNA sequences used in the Examples are

```
Chlamydia trachomatis G/SotonG1 plasmid pSotonG1 complete sequence
(GenBank: HE603235.1)
SEQ ID No. 7:
    1  tttgcaactc ttggtggtag actttgcaac tcttggtggt agactttgca actcttggtg 61  gtagacttgg tcataatgga cttttgttaa aaaatttctt aaaatcttag agctccgatt 121  ttgaatagct ttggttaaga aaatgggctc gatggctttc cataaaagta gattgttctt 181  aactttgg gacgcgtcgg aaatttggtt atctacttta tctcatctaa ctagaaaaaa 241  ttatgcgtct gggattaact ttcttgtttc tttagagatt ctggatttat cggaaacctt 301  gataaaggct atttctcttg accacagcga atctttgttt aaaatcaagt ctctagatgt 361  ttttaatgga aaagtcgttt cagaggcctc taaacaggct agagcggcat gctacatatc 421  tttcacaaag tttttgtata gattgaccaa gggatatatt aaaccccgcta ttccattgaa 481  agattttgga aacactacat tttttaaaat ccgagacaaa atcaaaacag aatcgatttc 541  taagcaggaa tggacagttt ttttgaagc gctccggata gtgaattata gagactattt 601  aatcggtaaa ttgattgtac aagggatccg taagttagac gaaattttgt ctttgcgcac 661  agacgatcta ttttttgcat ccaatcagat ttcctttcgc attaaaaaaa gacagaataa 721  agaaaccaaa attctaatca catttcctat cagcttaatg gaagagttgc aaaaatacac 781  ttgtgggaga aatgggagag tatttgtttc taaaataggg attcctgtaa caacaagtca
```

-continued

```
 841   ggttgcgcat aattttaggc ttgcagagtt ccatagtgct atgaaaataa aaattactcc
 901   cagagtactt cgtgcaagcg ctttgattca tttaaagcaa ataggattaa aagatgagga
 961   aatcatgcgt atttcctgtc tctcatcgag acaaagtgtg tgttcttatt gttctgggga
1021   agaggtaagt cctctagtac aaacacccac aatattgtga tataattaaa attatattca
1081   tattctgttg ccagaaaaaa cacctttagg ctatattaga gccatcttct ttgaagcgtt
1141   gtcttctcga gaggatttat cgtacgcaaa tatcatcttt gcggttgcgt gtcccgtgac
1201   cttcattatg tcggagtctg agcaccctag gcgtttgtac tccgtcacag cggttgctcg
1261   aagcacgtgc ggggttatct taaagggat tgcagcttgt agtcctgctt gagagaacgt
1321   gcgggcgatt tgccttaacc ccaccatttt tccggagcga gttacgaaga caaaacctct
1381   tcgttgaccg atgtactctt gtagaaagtg cataaacttc tgaggataag ttataataat
1441   cctctttct gtctgacggt tcttaagctg ggagaaagaa atggtagctt gttggaaaca
1501   aatctgacta atctccaagc ttaagacttc agaggagcgt ttacctcctt ggagcattgt
1561   ctgggcgatc aaccaatccc gggcgttgat ttttttagc tcttttagga aggatgctgt
1621   ttgcaaactg ttcatcgcat ccgttttac tatttccctg gttttaaaaa atgttcgact
1681   attttcttgt ttagaaggtt gcgctatagc gactattcct tgagtcatcc tgtttaggaa
1741   tcttgttaag gaaatatagc ttgctgctcg aacttgttta gtaccttcgg tccaagaagt
1801   cttggcagag gaaacttttt taatcgcatc taggattaga ttatgattta aagggaaaa
1861   ctcttgcaga ttcatatcca aagacaatag accaatcttt tctaaagaca aaaagatcc
1921   tcgatatgat ctacaagtat gtttgttgag tgatgcggtc caatgcataa taacttcgaa
1981   taaggagaag cttttcatgc gtttccaata ggattcttgg cgaatttta aaacttcctg
2041   ataagacttt tcgctatatt ctaacgacat ttcttgctgc aaagataaaa tccctttacc
2101   catgaaatcc ctcgtgatat aacctatccg caaaatgtcc tgattagtga ataatcagg
2161   ttgttaacag gatagcacgc tcggtatttt tttatataaa catgaaaact cgttccgaaa
2221   tagaaaatcg catgcaagat atcgagtatg cgttgttagg taaagctctg atatttgaag
2281   actctactga gtatattctg aggcagcttg ctaattatga gtttaagtgt tcccatcata
2341   aaaacatatt catagtattt aaatacttaa aagacaatgg attacctata actgtagact
2401   cggcttggga agagcttttg cggcgtcgta tcaaagatat ggacaaatcg tatctcgggt
2461   taatgttgca tgatgcttta tcaaatgaca agcttagatc cgtttctcat acggttttcc
2521   tcgatgattt gagcgtgtgt agcgctgaag aaaatttgag caatttcatt ttccgctcgt
2581   ttaatgagta caatgaaaat ccattgcgta gatctccgtt tctattgctt gagcgtataa
2641   agggaaggct tgatagtgct atagcaaaga cttttttctat tcgcagcgct agaggccggt
2701   ctatttatga tatattctca cagtcagaaa ttggagtgct ggctcgtata aaaaaaagac
2761   gagcagcgtt ctctgagaat caaaattctt tctttgatgg cttcccaaca ggatacaagg
2821   atattgatga taaaggagtt atcttagcta aaggtaattt cgtgattata gcagctaggc
2881   catctatagg gaaaacagct ttagctatag acatggcgat aaatcttgcg ttactcaac
2941   agcgtagagt tggtttccta tctctagaaa tgagcgcagg tcaaattgtt gagcggattg
3001   ttgctaattt aacaggaata tctggtgaaa aattacaaag aggggatctc tctaaagaag
3061   aattattccg agtggaagaa gctggagaaa cagttagaga atcacatttt tatatctgca
3121   gtgatagtca gtataagctt aatttaatcg cgaatcagat ccggttgctg agaaaagaag
3181   atcgagtaga cgtaatattt atcgattact tgcagttgat caactcatcg gttggagaaa
3241   atcgtcaaaa tgaaatagca gatatatcta gaaccttaag aggtttagcc tcagagctaa
```

-continued

```
3301  acattcctat agtttgttta tcccaactat ctagaaaagt tgaggataga gcaaataaag
3361  ttcccatgct ttcagatttg cgagacagcg gtcaaataga gcaagacgca gatgtgattt
3421  tgtttatcaa taggaaggaa tcgtcttcta attgtgagat aactgttggg aaaaatagac
3481  atggatcggt tttctcttcg gtattacatt tcgatccaaa aattagtaaa ttctccgcta
3541  ttaaaaaagt atggtaaatt atagtaactg ccacttcatc aaaagtccta tccaccttga
3601  aaatcagaag tttggaagaa gacctggtca atctattaag atatctccca aattggctca
3661  aaatgggatg gtagaagtta taggtcttga ttttctttca tctcattacc atgcattagc
3721  agctatccaa agattactga ccgcaacgaa ttacaagggg aacacaaaag gggttgtttt
3781  atccagagaa tcaaatagtt ttcaatttga aggatggata ccaagaatcc gttttacaaa
3841  aactgaattc ttagaggctt atggagttaa gcggtataaa acatccagaa ataagtatga
3901  gtttagtgga aaagaagctg aaactgcttt agaagccttg taccatttag acatcaacc
3961  gttttttaata gtggcaacta gaactcgatg gactaatgga acacaaatag tagaccgtta
4021  ccaaactctt tctccgatca ttaggattta cgaaggatgg gaaggtttaa ctgacgaaga
4081  aaatatagat atagacttaa cacctttttaa ttcaccatct acacggaaac ataaaggatt
4141  cgttgtagag ccatgtccta tcttggtaga tcaaatagaa tcctactttg taatcaagcc
4201  tgcaaatgta taccaagaaa taaaaatgcg tttcccaaac gcatcaaagt atgcttacac
4261  atttatcgac tgggtgatta cagcagctgc gaaaaagaga cgaaaattaa ctaaggataa
4321  ttcttggcca gaaaacttgt tattaaacgt taacgttaaa agtcttgcat atattttaag
4381  gatgaatcgg tacatctgta caaggaactg gaaaaaaatc gagttagcta tcgataaatg
4441  tatagaaatc gccattcagc ttggctggtt atctagaaga aaacgcattg aatttctgga
4501  ttcttctaaa ctctctaaaa aagaaattct atatctaaat aaagagcgct tgaagaaat
4561  aactaagaaa tctaaagaac aaatggaaca agaatctatt aattaatagc aggcttgaaa
4621  ctaaaaacct aatttattta aagctcaaaa taaaaagag ttttaaaatg ggaaattctg
4681  gtttttattt gtataacact gaaaactgcg tctttgctga taatatcaaa gttgggcaaa
4741  tgacagagcc gctcaaggac cagcaaataa tccttgggac aaaatcaaca cctgtcgcag
4801  ccaaaatgac agcttctgat ggaatatctt taacagtctc caataattca tcaaccaatg
4861  cttctattac aattggtttg gatgcggaaa aagcttacca gcttattcta gaaaagttgg
4921  gaaatcaaat tcttgatgga attgctgata ctattgttga tagtacagtc caagatattt
4981  tagacaaaat cacaacagac ccttctctag gtttgttgaa agcttttaac aactttccaa
5041  tcactaataa aattcaatgc aacgggttat tcactcccag taacattgaa actttattag
5101  gaggaactga aataggaaaa ttcacagtca cacccaaaag ctctgggagc atgttcttag
5161  tctcagcaga tattattgca tcaagaatgg aaggcggcgt tgttctagct ttggtacgag
5221  aaggtgattc taagccctgc gcgattagtt atggatactc atcaggcgtt cctaatttat
5281  gtagtctaag aaccagcatt actaatacag gattgactcc aacaacgtat tcattacgtg
5341  taggcggttt agaaagcggt gtggtatggg ttaatgccct ttctaatggc aatgatattt
5401  taggaataac aaatacttct aatgtatctt ttttggaagt aatacctcaa acaaacgctt
5461  aaacaatttt tattggattt ttcttatagg ttttatattt agagaaaaca gttcgaatta
5521  cggggtttgt tatgcaaaat aaaagaaaag tgagggacga ttttattaaa attgttaaag
5581  atgtgaaaaa agatttcccc gaattagacc taaaaatacg agtaaacaag gaaaaagtaa
5641  cttttcttaaa ttctccctta gaactctacc ataaaagtgt ctcactaatt ctaggactgc
```

-continued

```
5701  ttcaacaaat agaaaactct ttaggattat tcccagactc tcctgttctt gaaaaattag 5761  aggataacag tttaaagcta aaaaaggctt tgattatgct tatcttgtct agaaaagaca 5821  tgttttccaa ggctgaatag acaacttact ctaacgttgg agttgatttg cacaccttag 5881  ttttttgctc ttttaaggga ggaactggaa aaacaacact ttctctaaac gtgggatgca 5941  acttggccca attttttaggg aaaaaagtgt tacttgctga cctagacccg caatccaatt 6001  tatcttctgg attgggggct agtgtcagaa ataaccaaaa aggcttgcac gacatagtat 6061  acaaatcaaa cgatttaaaa tcaatcattt gcgaaacaaa aaaagatagt gtggacctaa 6121  ttcctgcatc attttatcc gaacagttta gagaattgga tattcataga ggacctagta 6181  acaacttaaa gttatttctg aatgagtact gcgctccttt ttatgacatc tgcataatag 6241  acactccacc tagcctagga gggttaacga agaagctttt tgttgcagga gacaaattaa 6301  ttgcttgttt aactccagaa ccttttttcta ttctagggtt acaaaagata cgtgaattct 6361  taagttcggt cggaaaacct gaagaagaac acattcttgg aatagctttg tcttttttggg 6421  atgatcgtaa ctcgactaac caaatgtata tagacattat cgagtctatt tacaaaaaca 6481  agcttttttc aacaaaaatt cgtcgagata tttctctcag ccgttctctt cttaaagaag 6541  attctgtagc taatgtctat ccaaattcta gggccgcaga agatattctg aagttaacgc 6601  atgaaatagc aaatattttg catatcgaat atgaacgaga ttactctcag aggacaacgt 6661  gaacaaacta aaaaagaag cggatgtctt ttttaaaaaa aatcaaactg ccgcttctct 6721  agattttaag aagacacttc cttccattga actattctca gcaactttga attctgagga 6781  aagtcagagt ttggatcgat tattttatc agagtcccaa aactattcgg atgaagaatt 6841  ttatcaagaa gacatcctag cggtaaaact gcttactggt cagataaaat ccatacagaa 6901  gcaacacgta cttcttttag gagaaaaaat ctataatgct agaaaaatcc tgagtaagga 6961  tcacttctcc tcaacaactt tttcatcttg gatagagtta gtttttagaa ctaagtcttc 7021  tgcttacaat gctcttgcat attcgagct ttttataaac ctccccaacc aaactctaca 7081  aaaagagttt caatcgatcc cctataaatc cgcatatatt ttggccgcta gaaaaggcga 7141  tttaaaaacc aaggtcgatg tgatagggaa agtatgtgga atgtcgaact catcggcgat 7201  aagggtgttg gatcaatttc ttccttcatc tagaaacaaa gacgttagag aaacgataga 7261  taagtctgat ttagagaaga atcgccaatt atctgatttc ttaatagaga tacttcgcat 7321  catatgttcc ggagtttctt tgtcctccta taacgaaaat cttctacaac agctttttga 7381  acttttttaag caaaagagct gatcctccgt cagctcatat atatatttat tatatatata 7441  tttatttagg gatttgattt tacgagagag a
```

*Neisseria gonorrhoeae* partial porA gene for class 1 outer membrane protein, isolate GC3 (GenBank: HE681886.1)
SEQ ID No. 8:

```
  1  gccggcggcg gcgcgacccg ttggggcaat agggaatcct ttgtcggctt ggcaggcgaa 61  ttcggcacgc tgcgcgccgg ccgcgttgcg aatcagtttg acgatgccag ccaagccatt 121  gatccttggg acagcaacaa tgatgtggct tcgcaattgg gtattttcaa acgccacgac 181  gatatgccgg tttccgtacg ctacgactcc ccggactttt ccgtttcag cggcagcgtc 241  caattcgttc cggctcaaaa cagcaagtcc gcctatacgc cggctcattg gactactgtg 301  tataacacta acggtactac tactactttc gttccggctg ttgtcggcaa gcccggatcg 361  gatgtgtatt atgccggtct gaattacaaa aatggcggtt ttgccgggaa ctatgccttt 421  aaatatgcga gacacgccaa tgtcggacgt aatgcttttg agttgttctt gctcggcagt 481  gggagtgatg aagccaaagg taccgatccc ttgaaaaacc atcaggtaca ccgcctgacg
```

-continued

```
541  ggcggctatg gggaaggcgg cttgaatctc gccttggcgg ctcagttgga tttgtctgaa 601  aatgccgaca aaaccaaaaa cagtacgacc gaaattgccg ccactgcttc ctaccgcttc 661  ggtaatacag tcccgcgcat cagctatgcc catggtttcg actttgtcga acgcagtcag 721  aaacgcgaac ataccagcta tga
```

Neisseria gonorrhoeae glutamine synthetase (glnA) gene, glnA-14 allele, partial cds
(GenBanK: AF520262.1)
SEQ ID No. 9:

```
   1  cccgctttgt cgatttgcgc ttcaccgata ccaaaggcaa gcagcaccac tttaccgtgc 61  ctgcgcgcat cgtgttggaa gaccccgaag agtggtttga aaacggaccg gcgtttgacg 121  gctcgtccat cggcggctgg aaaggcattg aggcttccga tatgcagctg cgtcccgatg 181  cgtccacagc cttcgtcgat cctttttatg atgatgttac cgtcgtcatt acctgcgacg 241  tcatcgaccc tgccgacggt cagggttacg accgcgaccc gcgctccatc gcacgccgcg 301  ccgaagccta tttgaaatct tccggtatcg gcgacaccgc ctatttcggc cccgaacccg 361  aattcttcgt cttcgacggc gtagaatttg aaaccgacat gcacaaaacc cgttacgaaa 421  tcacgtccga agcggcgcg tgggcaagcg gcctgcatat ggacggtcaa acaccggcc 481  accgcccgc cgtcaaaggc ggctacgcgc ccgtcgcgcc gattgactgc ggtcaagatt 541  tgcgctccgc catggtgaac attttggaag gactcggcat cgaagtcgaa gtccaccaca 601  gcgaagtcgg taccggcagc caaatggaaa tcggcacccg tttcgccact ttggtcaaac 661  gcgccgacca aacccaagat atgaaatacg tcatccaaaa cgttgcccac aatttcggca 721  aaaccgccac ctttatgccc aaaccgatta tgggcgacaa cggcagcggt atgcacgtcc 781  accaatccat ttggaaagac ggtcaaaacc tgttcgcagg cgacggctat gccggtttgt 841  ccgataccgc gctctactac atcggcggca tcatcaaaca cgccaaagcc ctgaacgcga 901  ttaccaatcc gtccaccaac tcctacaaac gcctcgtgcc gcactttgaa gcaccgacca 961  aattggccta ttccgccaaa aaccgttccg cttccatccg tatcccgtct gtgaacagca 1021  gcaaggcgcg ccgcatcgaa gcgcgtttcc ccgacccgac cgccaacccg tatttggcat 1081  ttgccgccct gctgatggcc ggtttggacg gcattcaaaa caaaatccat ccgggcgacc 1141  ctgccgataa aaacctgtac gacctgccgc cggaagaaga gcgcgctcgtc ccgaccgtct 1201  gcgcttcttt ggaagaagca cttgccgccc tcaaggtcga ccacgaattc ctgctgcgcg 1261  gcggcgtgtt cagcaaagac tggatcgaca gctacatcgc ctttaaagag gaagatgtcc 1321  gccgcatccg tatggcgccg cacccgctgg aatttg
```

The primer sequences used in the LAMP reaction are as follows:

CT plasmid
F3
(SEQ ID No. 10)
TCTACAAGAGTACATCGGTCA

B3
(SEQ ID No. 11)
TGAAGCGTTGTCTTCTCG

FIP
(SEQ ID No. 12)
GCAGCTTGTAGTCCTGCTTGAGTCTTCGTAACTCGCTCC

BIP
(SEQ ID No. 13)
TCGAGCAACCGCTGTGACCCTTCATTATGTCGGAGTCTG

LF1
(SEQ ID No. 14)
CGGGCGATTTGCCTTAAC

LB1
(SEQ ID No. 15)
TACAAACGCCTAGGGTGC

GC porA7
F3
(SEQ ID No. 16)
ACCAAAACAGTACGACCGA

B3
(SEQ ID No. 17)
AAGTGCGCTTGGAAAAATCG

FIP
(SEQ ID No. 18)
ATGGGCATAGCTGATGCGCGAATTGCCGCCACTGCTTC

-continued

```
BIP
                                            (SEQ ID No. 19)
TCGACTTTGTCGAACGCAGTCAAATCGACACCGGCGATGA

LoopF1
                                            (SEQ ID No. 20)
GCGAACATACCAGCTATGATCAA GC glnA7
F3
                                            (SEQ ID No. 21)
TCATATCTTGGGTTTGGTCG B3
                                            (SEQ ID No. 22)
CTGCATATGGACGGTCAAA FiP
                                            (SEQ ID No. 23)
CGAAGTCCACCACAGCGAATTTGACCAAAGTGGCGAA BiP
                                            (SEQ ID No. 24)
CTTCGATGCCGAGTCCTTCCGATTGACTGCGGTCAAGAT LF
                                            (SEQ ID No. 25)
CAAATGGAAATCGGCACCC LB
                                            (SEQ ID No. 26)
ATGTTCACCATGGCGGAG
```

Buffer

The Applicant has developed a buffer system for use with the probes of the invention and is designated V6.21 (or V6.21p without V13 dye present) in the following Examples. The concentrations of the buffer components are after buffer reconstitution:

V6.21

4-10 mM dNTP's, 10 mM salt, 30 mM Tris pH8.8, 30 mM Trehalose, 1-8U Bst polymerase, Dye and 0.05% propanediol.

V6.21p 4-10 mM dNTP's, 10 mM salt, 30 mM Tris pH8.8, 30 mM Trehalose, 1-8U Bst polymerase, and 0.05% propanediol.

PCR

CT/GC detection in clinical samples by real-time PCR was performed using APTIMA CT/GC multiplex (Gen-Probe) according to the manufacturer's instructions.

Agarose Gel Electrophoresis

DNA electrophoresis was conducted in 1% agarose gel 1×TAE buffer at 100V. LAMP DNA products were vitalized with GelRed (Invitrogen) with transilluminator.

V6.21 and V6.21p buffer were developed by the Applicant. LAMP primers were obtained from Eurofins. Fluorophore-labelled oligonucleotides were purchased from Integrated DNA technologies. Tris buffer, agarose gel and PCR grade water were purchased from Sigma. CT and GC DNA standards were obtained from ATCC.

FIGURES

FIG. 1 is a schematic of DNA probe of the invention. The probe consists of an oligonucleotide with an internal cytosine conjugated with a defined fluorophore. The probe may be complementary to the internal region of the amplicon flanked by Fip and Bip primers or it may be a modified LoopF or LoopB primer internally labeled with a fluorophore.

Example 1

Figure 2B:
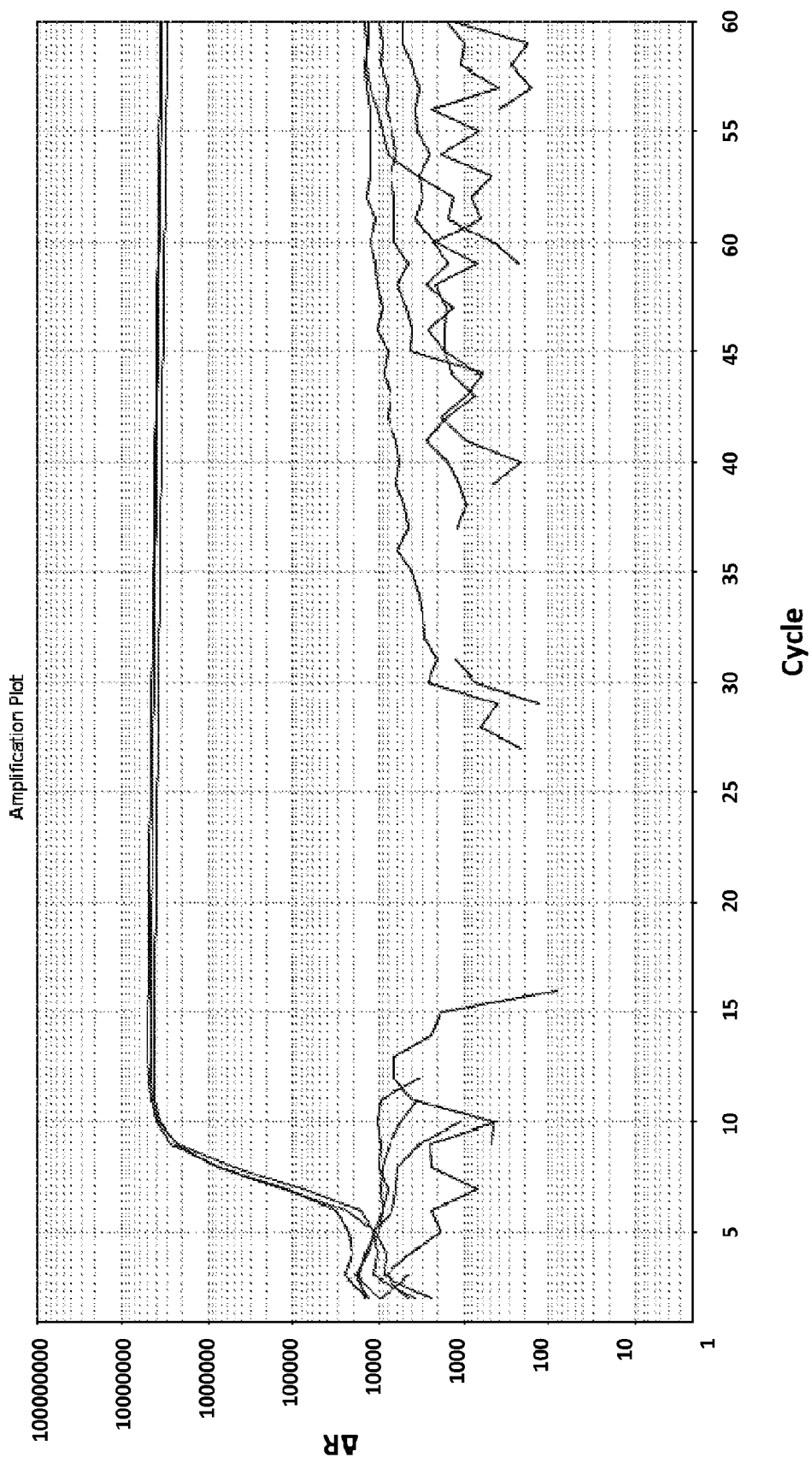
Figure 2E:
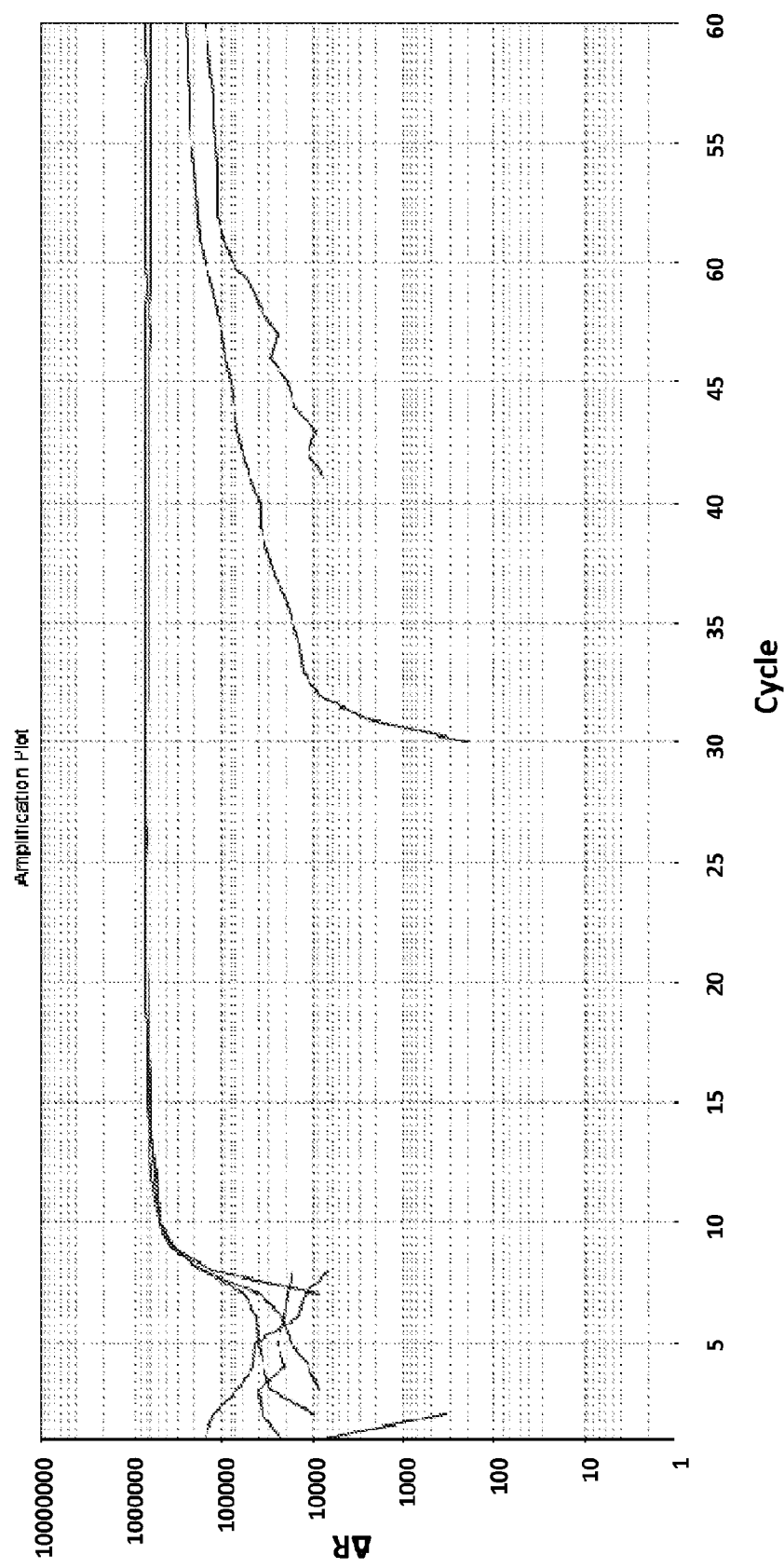
Figure 2F:
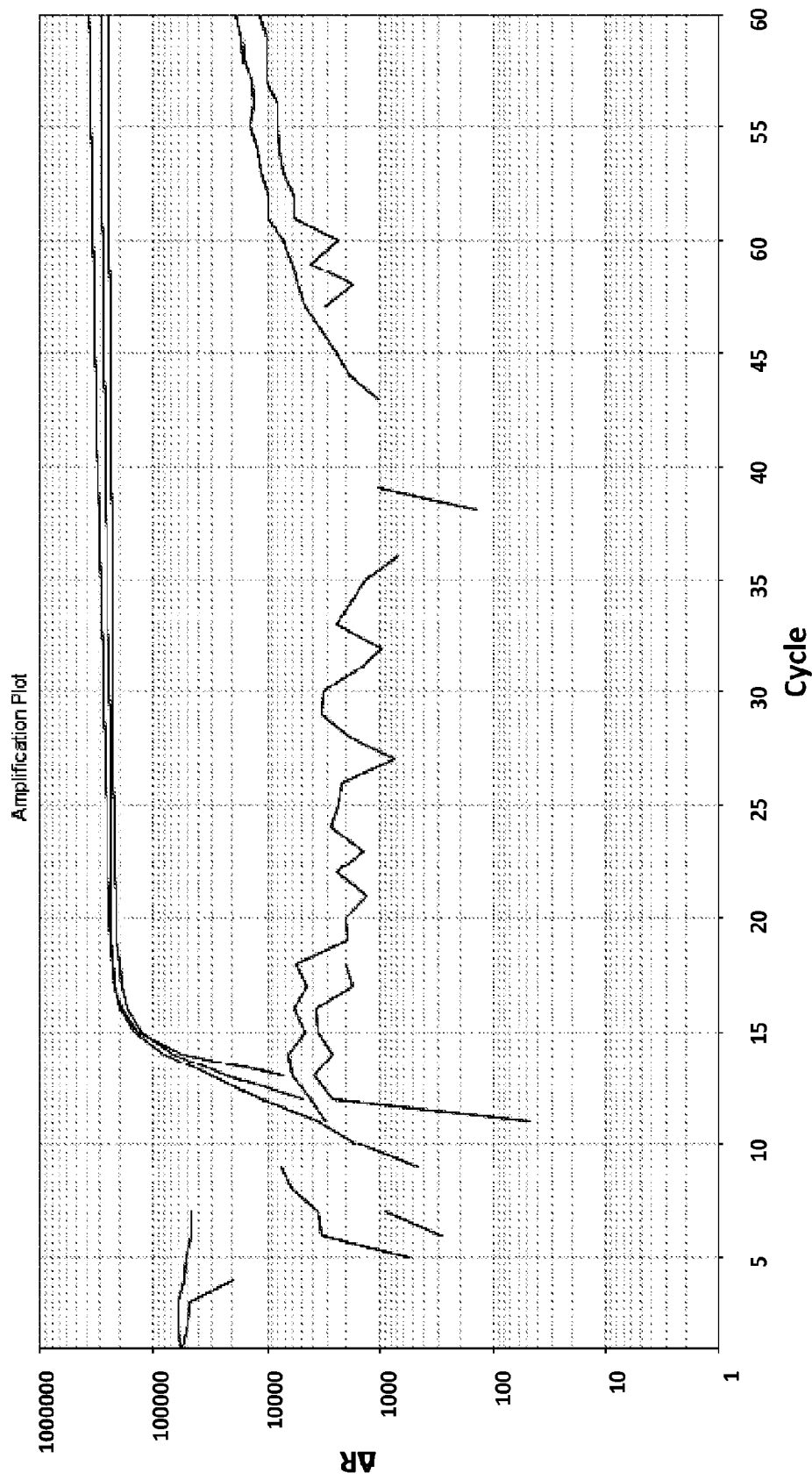

FIGS. 2A to 2F shows amplification plots generated with the CT PB1 (FIG. 2A and FIG. 2D), GC glnA7 (FIG. 2B and FIG. 2E) and GC porA7 (FIG. 2C and FIG. 2F) primers in V6.21 buffer containing V13 (FIGS. 2A, 2B and 2C) or V6.21p buffer without V13 dye (FIGS. 2D, 2E and 2F). The target sequences shown in SEQ ID NOs. 7 to 9 with CT PB1 internal probe conjugated with FAM, GC glnA7 loop probe conjugated with Joe and GC porA7 loop probe conjugated with Alexa546 respectively. All reactions were performed for 60 mins at a constant temperature of 63 C with ABI7500 machine.

Example 2

Figure 3A:
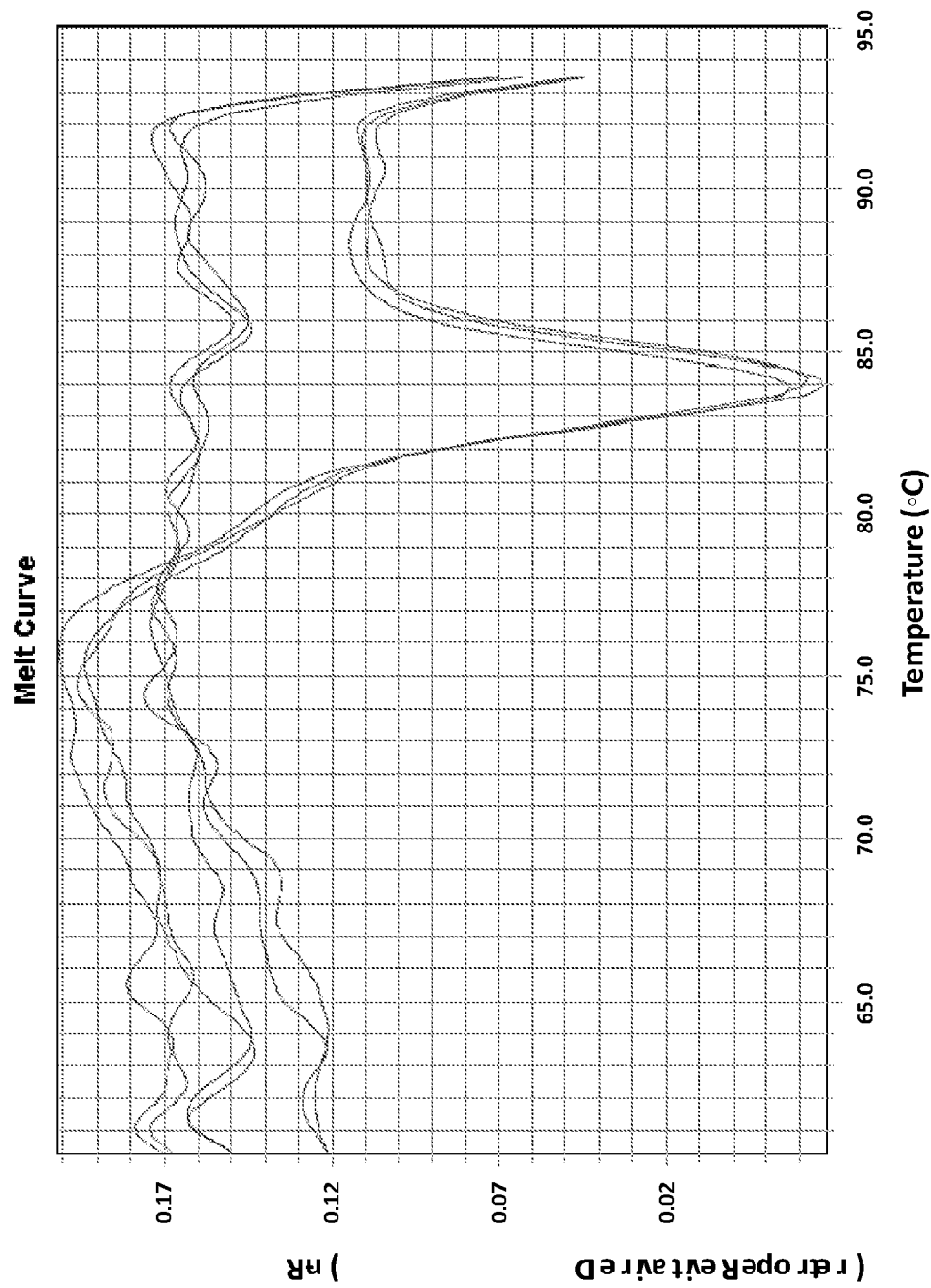
FIGS. 3A and 3B are melt curve analyses of LAMP products generated with CT PB1 primers in the presence of CT PB1 internal probe conjugated with FAM. 100 pg per reaction of ATTC CT DNA standard was used as a positive control. A—normalized reporter plot, B—derivative reporter plot.
Figure 3B:
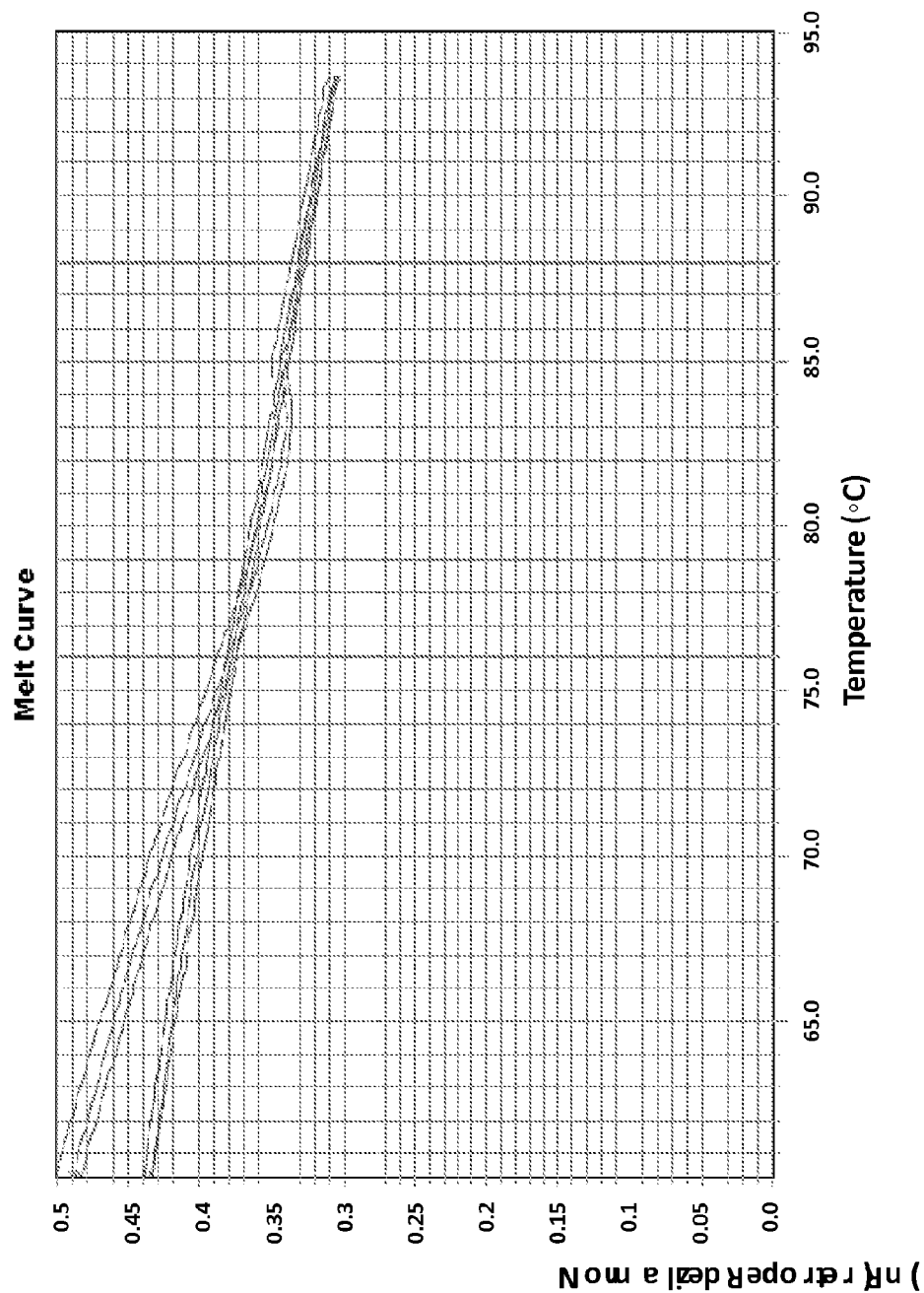

FIGS. 3A and 3B are melt curve analyses of LAMP products generated with CT PB1 primers in the presence of CT PB1 internal probe conjugated with FAM. 100 pg per reaction of ATTC CT DNA standard was used as a positive control. A—normalized reporter plot, B—derivative reporter plot. Melt curve plots were generated based on the readouts in FAM channel with ABI7500 machine.

Example 3

Figure 4A:
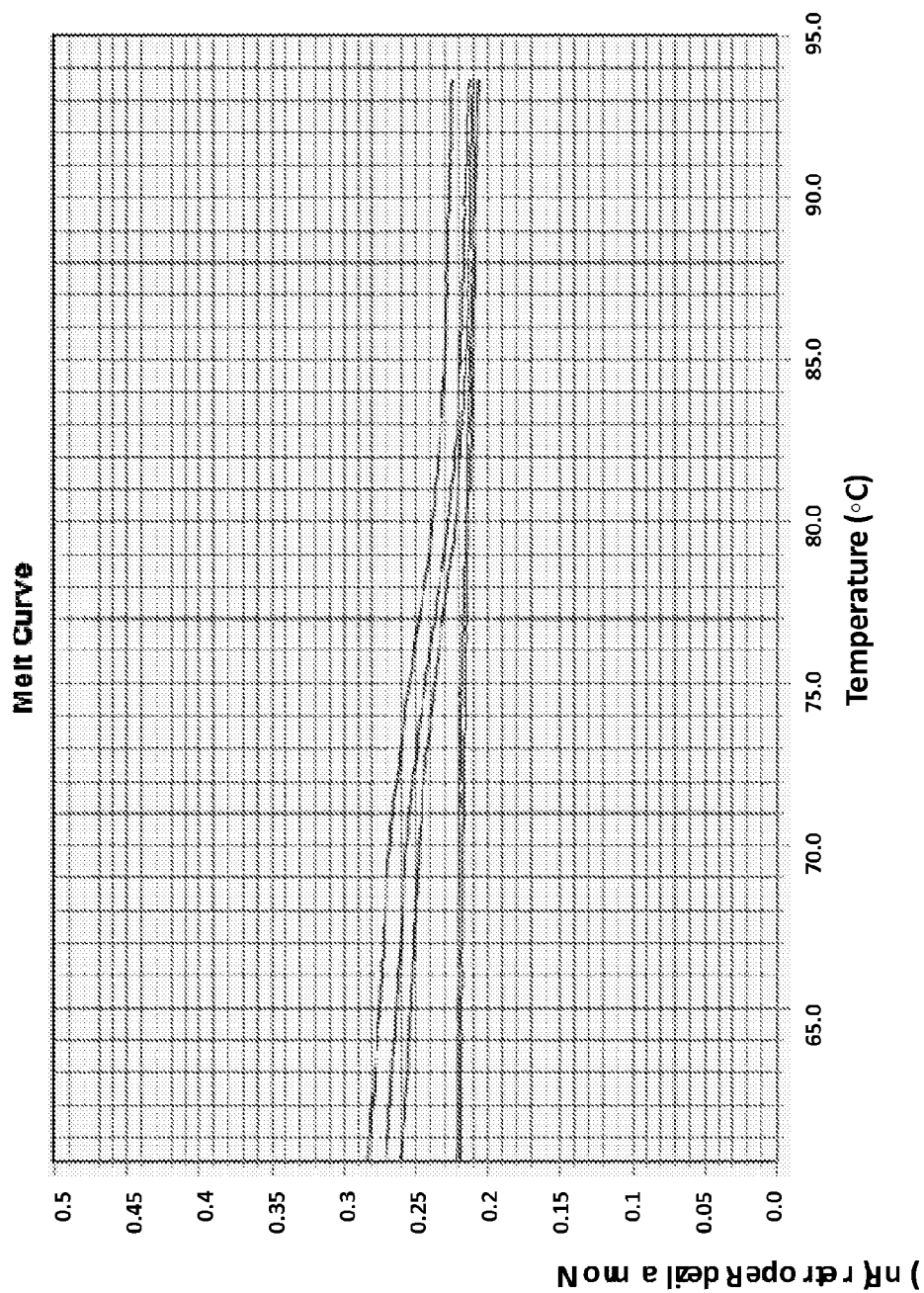
FIGS. 4A and 4B are melt curve analyses of LAMP product generated with GC glnA7 primers in the presence of GC glnA7 loop probe conjugated with JOE.
Figure 4B:
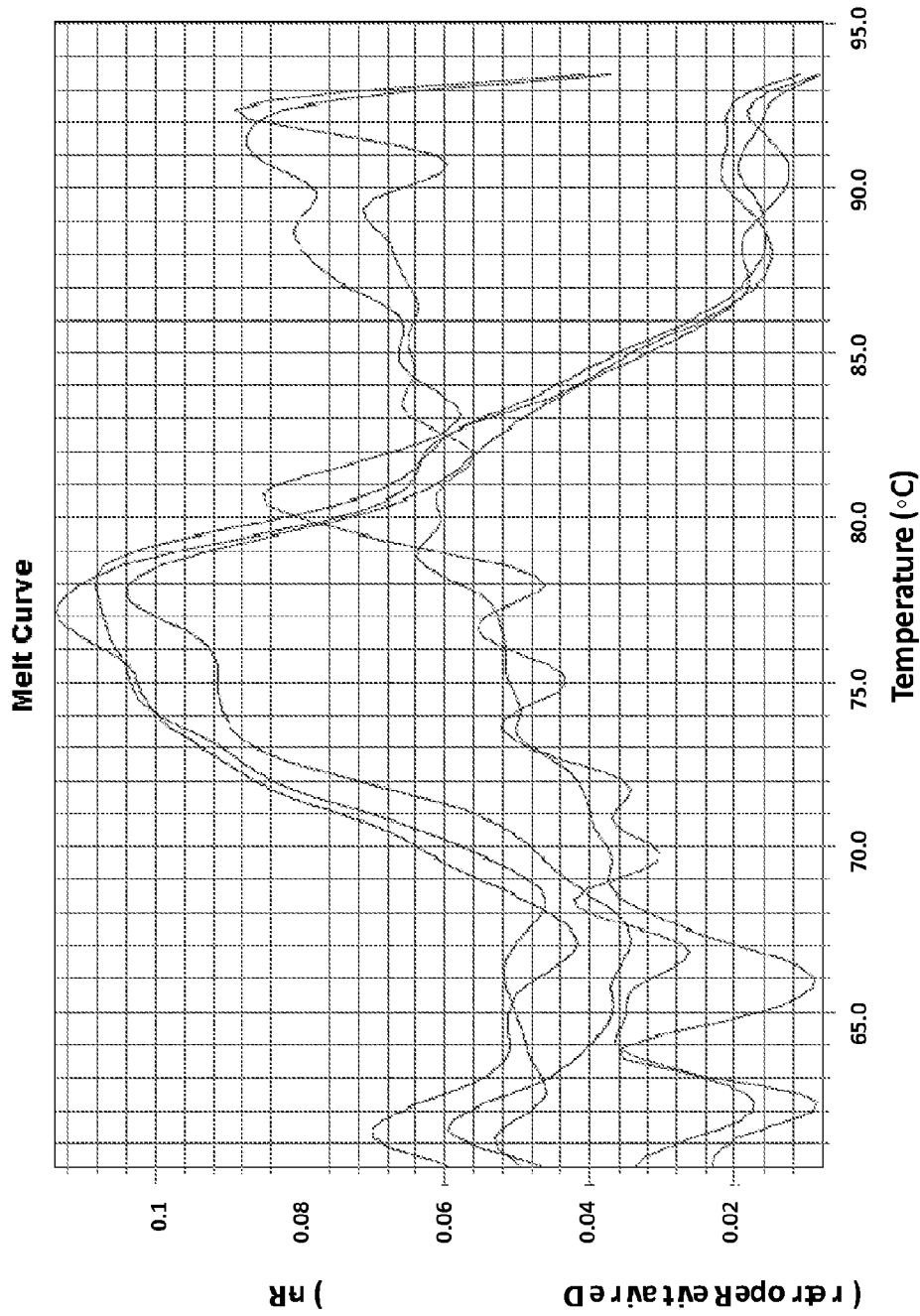

FIGS. 4A and B are melt curve analyses of LAMP product generated with GC glnA7 primers in the presence of GC glnA7 loop probe conjugated with JOE. 100 pg per reaction of ATTC GC DNA standard was used as a positive control. FIG. 4A shows a normalized reporter plot and FIG. 4B shows a derivative reporter plot. Melt curve plots were generated based on the readouts in JOE channel with ABI7500 machine.

Example 4

Figure 5A:
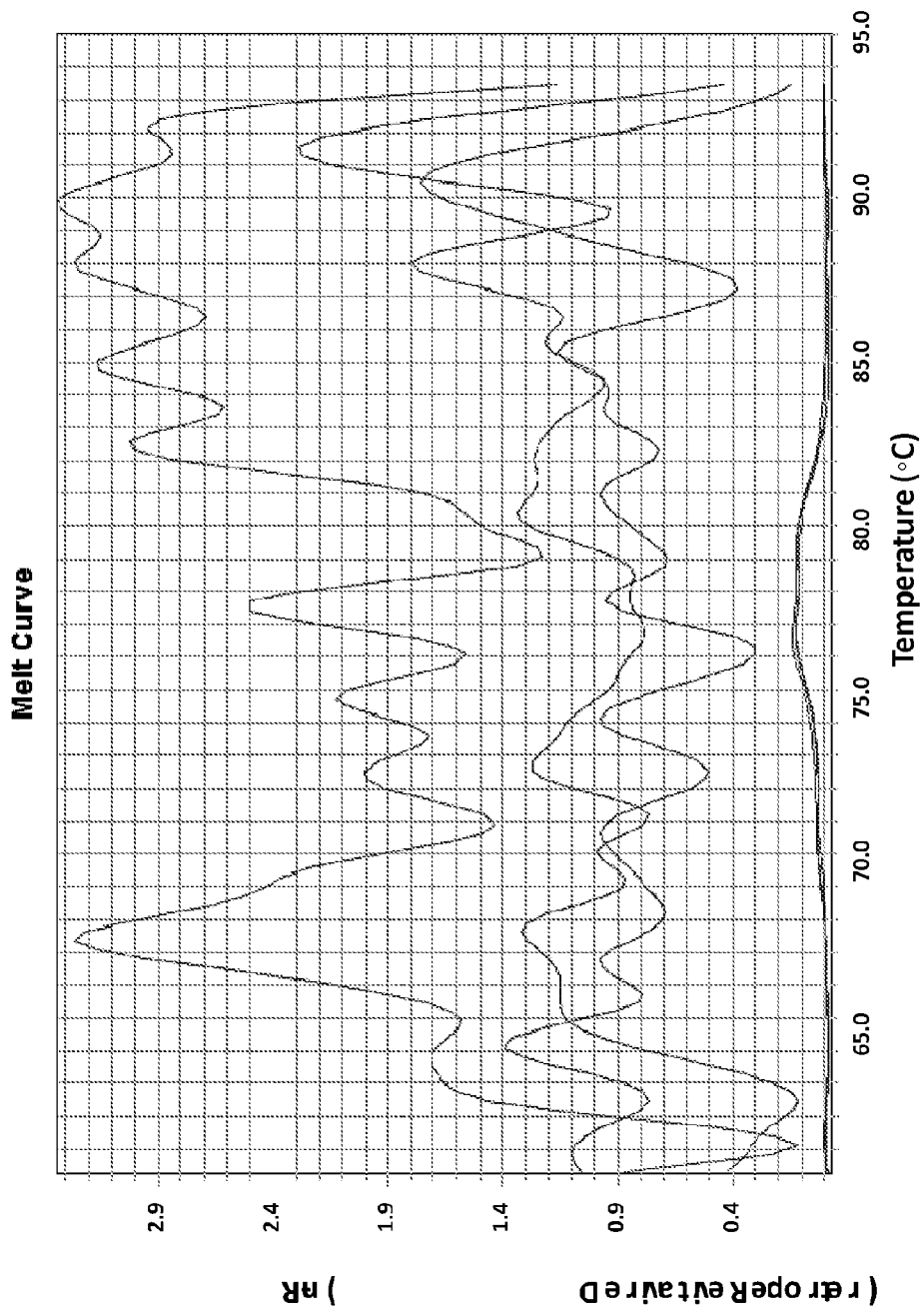
FIGS. 5A and 5B are melt curve analyses of LAMP product generated with GC porA7 primers in the presence of GC porA7 loop probe conjugated with ALEXA546. 100 pg per reaction of ATTC GC DNA standard was used as a positive control.
Figure 5B:
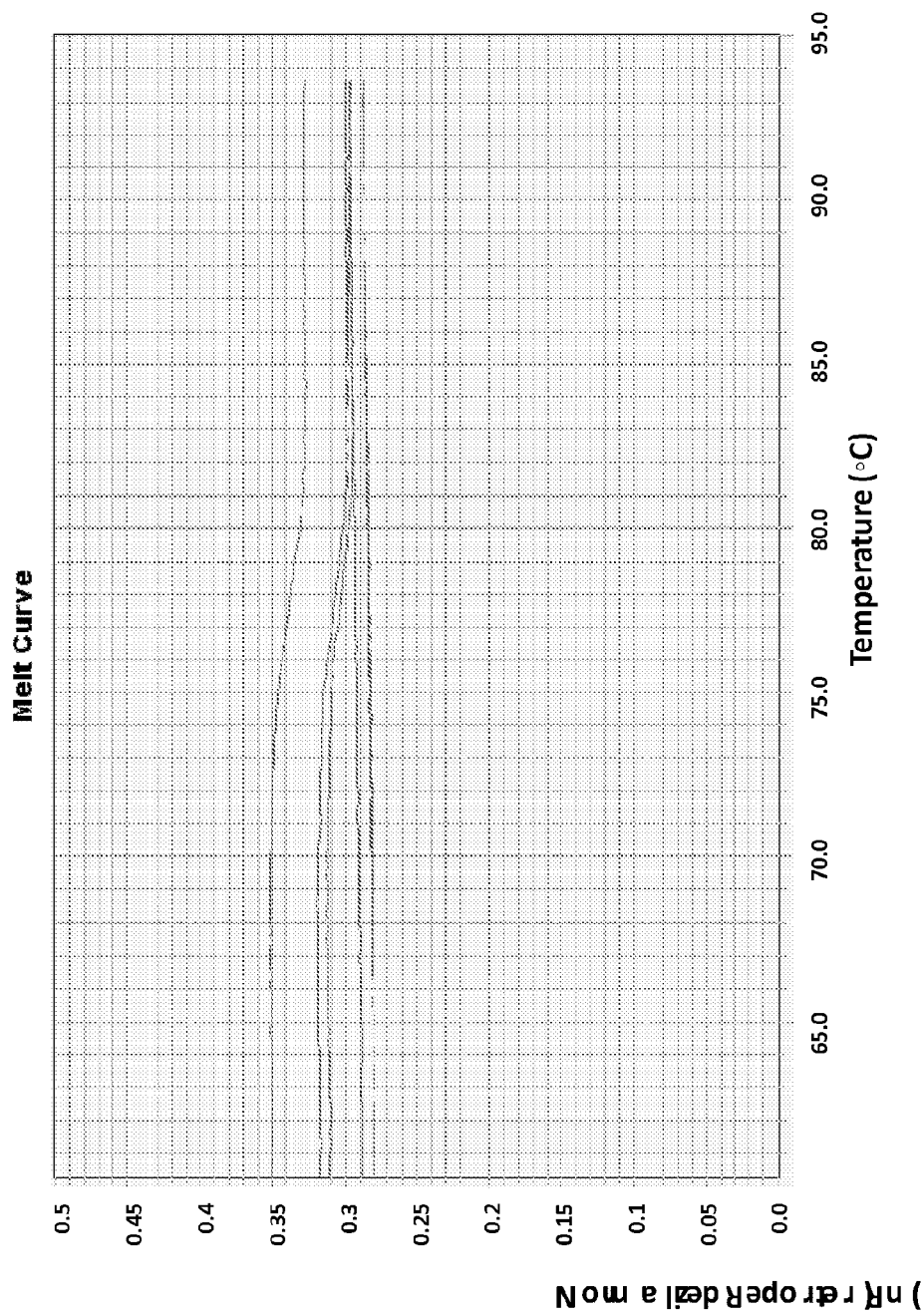

FIGS. 5A and 5B are melt curve analyses of LAMP product generated with GC porA7 primers in the presence of GC porA7 loop probe conjugated with ALEXA546. 100 pg per reaction of ATTC GC DNA standard was used as a positive control. FIG. 5A shows a normalized reporter plot, FIG. 4B shows a derivative reporter plot. Melt curve plots were generated based on the readouts in Cy3 channel with ABI7500 machine.

Example 5

FIGS. 6A to 6D show the results of a test to confirm the DNA product specificity with a probe of the invention in loop mediated isothermal amplification. The late amplification time of the false positives (more than 30 mins after the lowest target DNA concentration detectable in the LAMP reaction (100 fg GC DNA) indicates that the unspecific amplification may be a result of primer dimer formation. The standard melt curve analysis does not allow to distinguish between the specific and unspecific product in this LAMP reaction, but the unspecific product may be recognized with the probe of the invention. GC DNA was amplified with GC porA7 primers and visualized with V13 dye or GC porA7-ALEXA546 probe as appropriate.

Example 6

FIG. 7 shows the amplification plots generated with CT PB1 primers in V6.21 buffer containing V13 or V6.21p buffer without V13 dye but in the presence of CT PB1 terminal probe (complementary to loop region) with an internal C conjugated with FAM and 3' terminator (3'ddC). Despite a successful amplification of the target DNA confirmed by excitation of the V13 dye in the control reaction, CT PB1 probe with 3' terminator did not generate a positive signal.

Example 7

Figure 8B:
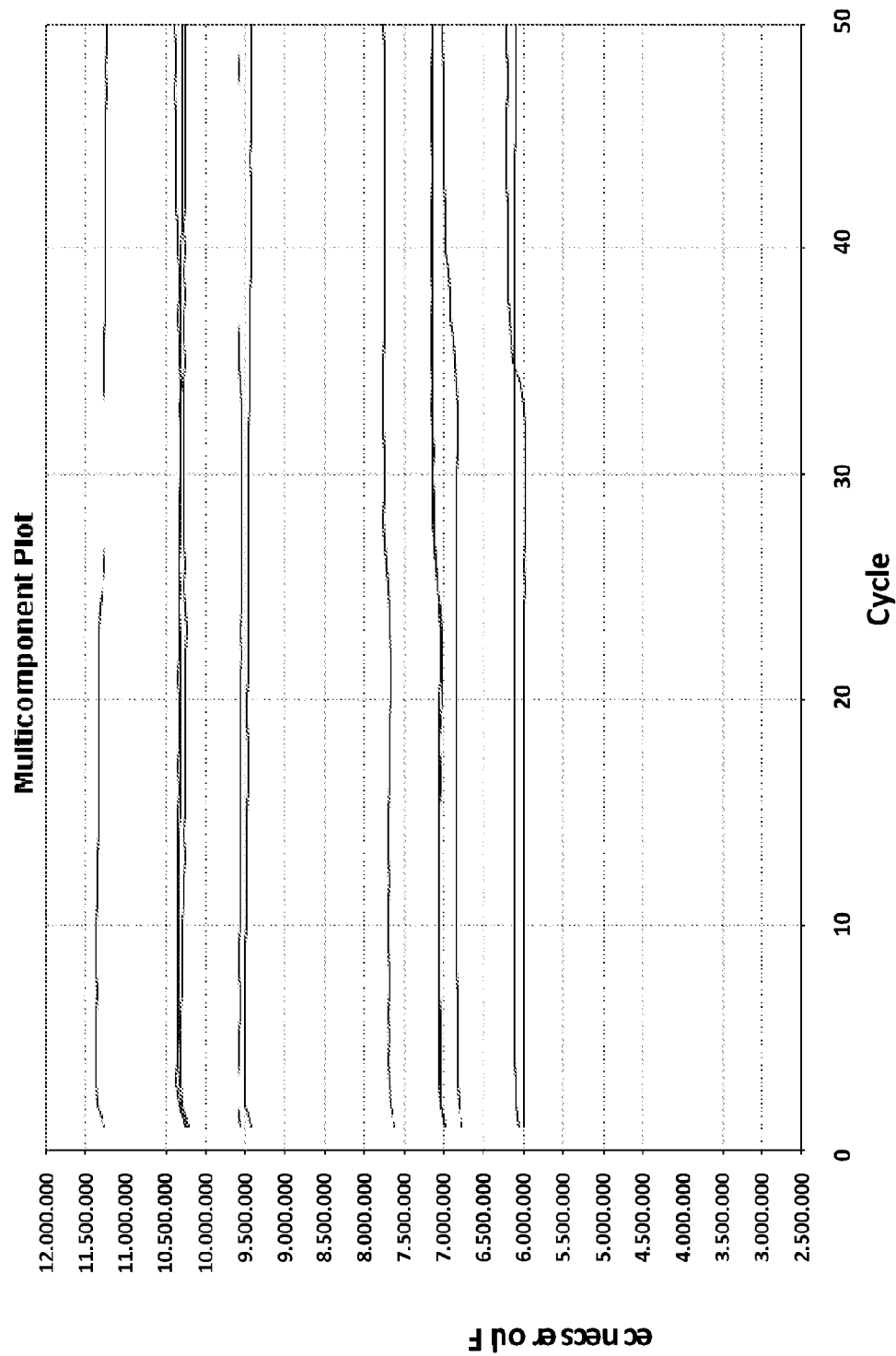

FIGS. 8A and 8B shows the amplification plots generated in V6.21p buffer containing ROX in the presence of CT PB1 primers and CT PB1 terminal probe with an internal cytosine conjugated with FAM (FIG. 8A), and universal primers and 3'UP probe with 3' terminal cytosine conjugated with FAM (FIG. 8B). The first line represents signals generated by ROX, and the second line corresponds to the signal generated in the FAM channel. Binding of the probe with an internally labeled C to the target DNA results in FAM excitation. Binding of the probe with a 3' end C labeled to the target does not alter the FAM excitation state.

Example 8

Figure 9B:
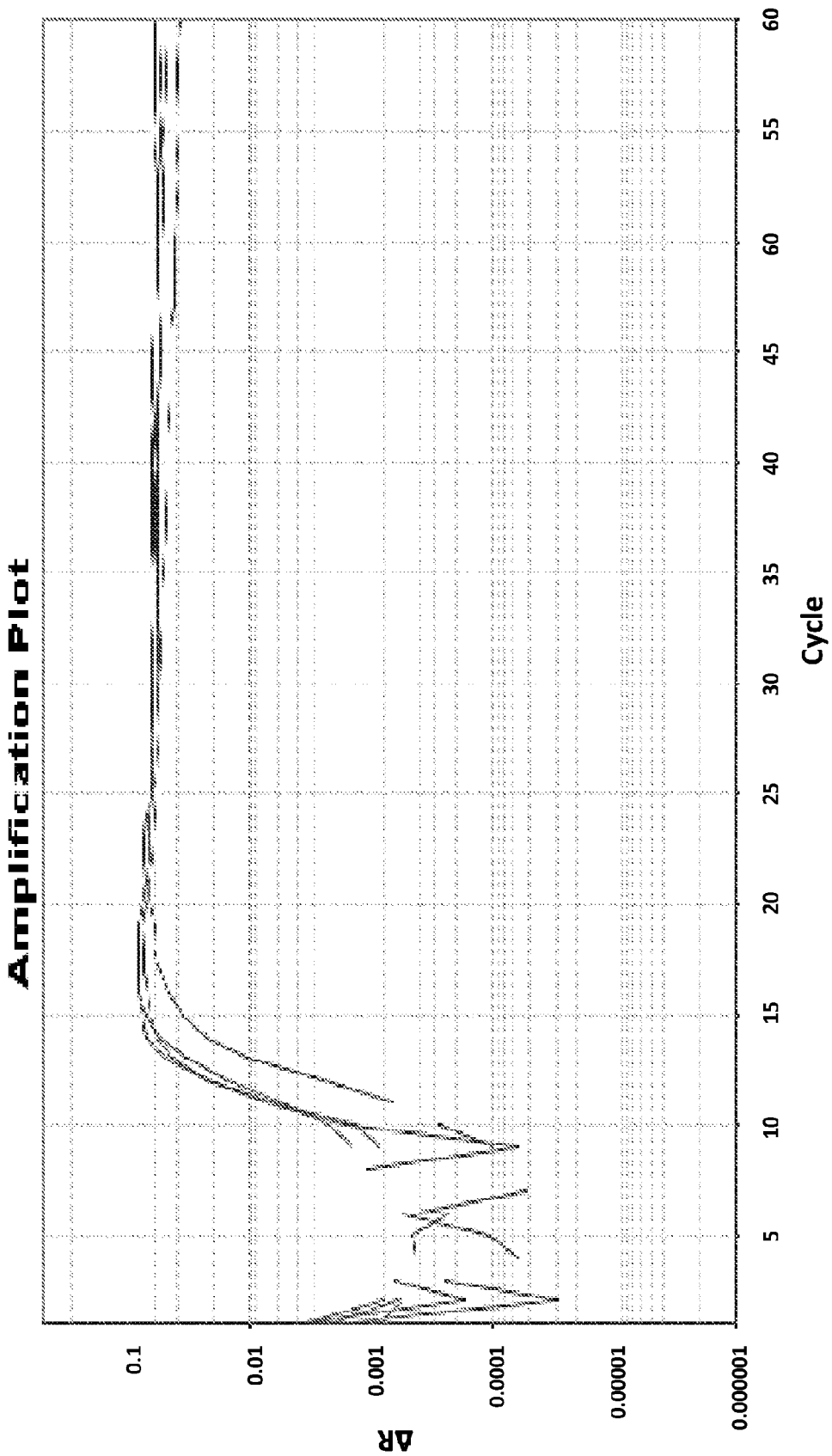

FIGS. 9A to 9C show the amplification plots generated with CT PB1 primers in V6.21p buffer without V13 in the presence of CT PB1 internal probe with an internal C conjugated with FAM and a reference dye (ROX). FIG. 9A show raw data, readouts from the FAM channel in the first line and from the ROX channel in a second line. FIG. 9B shows amplification plots (generated in FAM channel) normalized to ROX. FIG. 9C shows derivative reporter melt curve plots.

Example 9

Figure 10A:
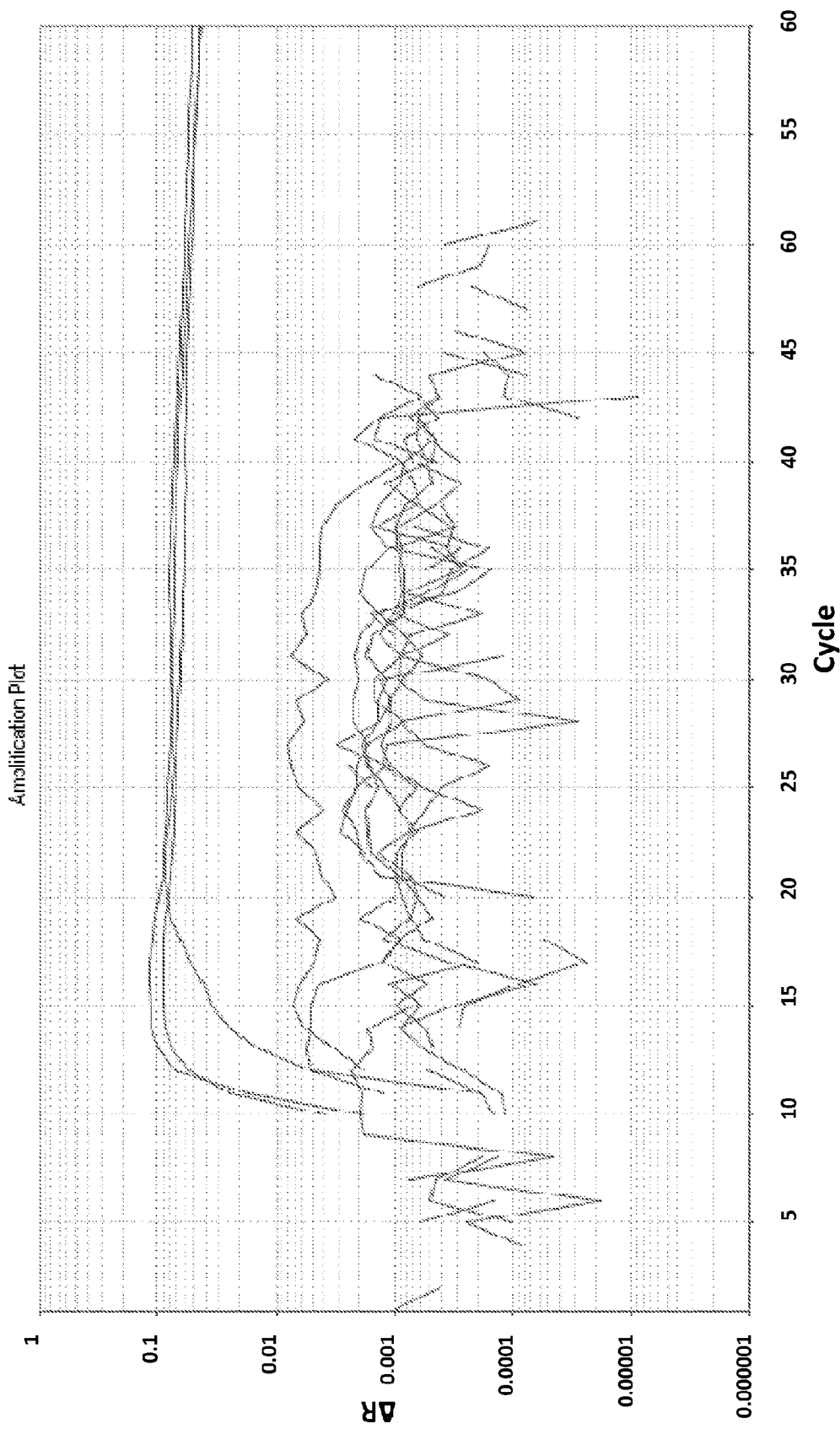
Figure 10B:
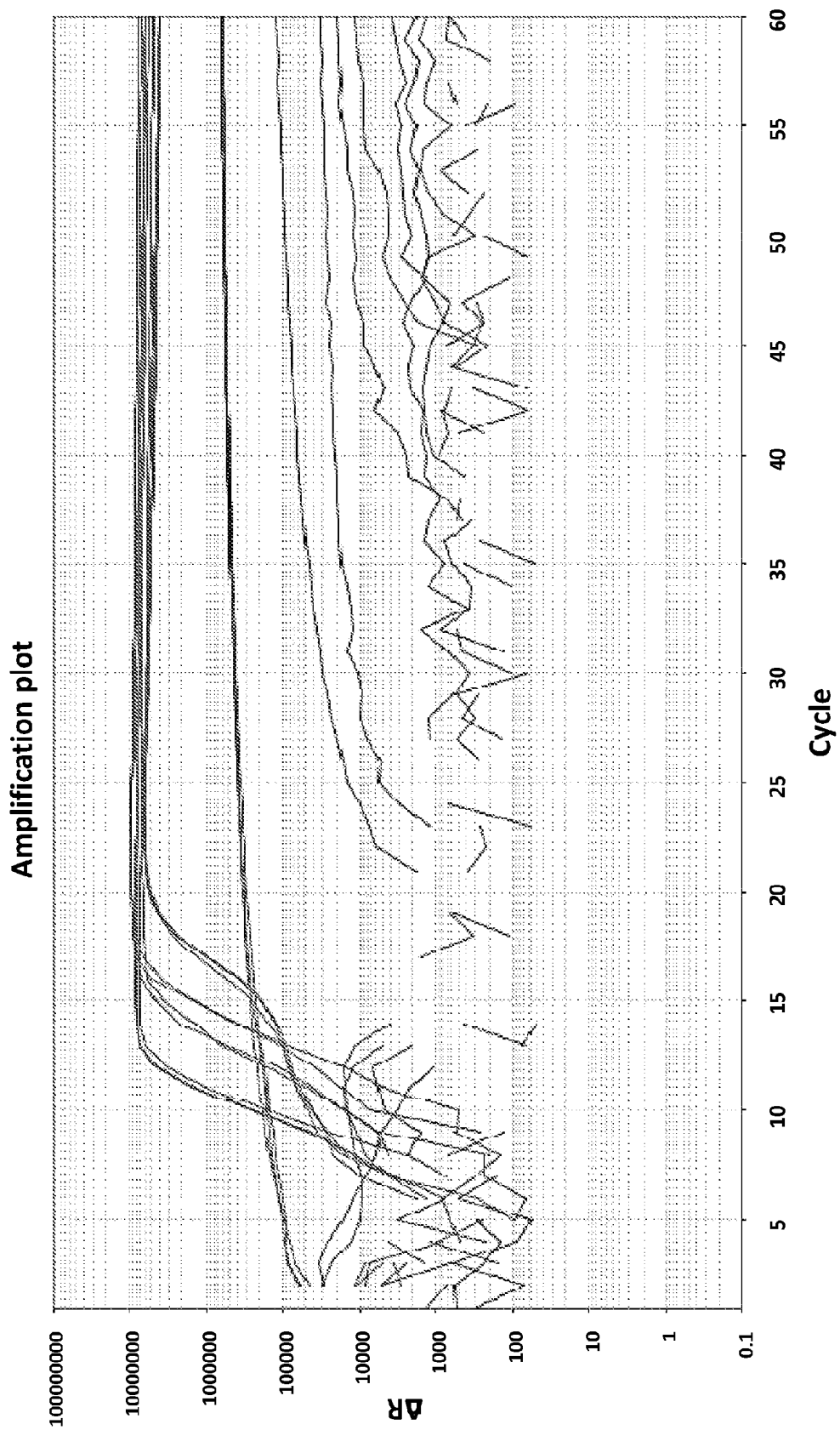

FIGS. 10A to 10C show the validation of CT PB1-FAM probe specificity. FIG. 10A shows amplification plots generated with CT PB1-FAM probe in the presence of CT DNA and CT primers. As a control, two sets of reactions were performed where unspecific genes, GC glnA7 and GC porA7 were amplified with the corresponding LAMP primers in the presence of CT PB1-FAM probe. In V6.21p buffer the amplification plots in the presence of CT PB1 probe in the FAM channel were generated only when CT DNA was present in the reaction and no signal was generated when unspecific genes (GC glnA7 and GC porA7) were amplified. No signal was also generated when an unspecific probe was used in a reaction where CT DNA was amplified with CT primers. FIG. 10C shows data obtained in an analogous experiment but conducted in V6.21 buffer containing an intercalating dye V31. FIG. 10C shows DNA products generated in the experiment described in FIG. 10A.

Example 10

Figure 11A:
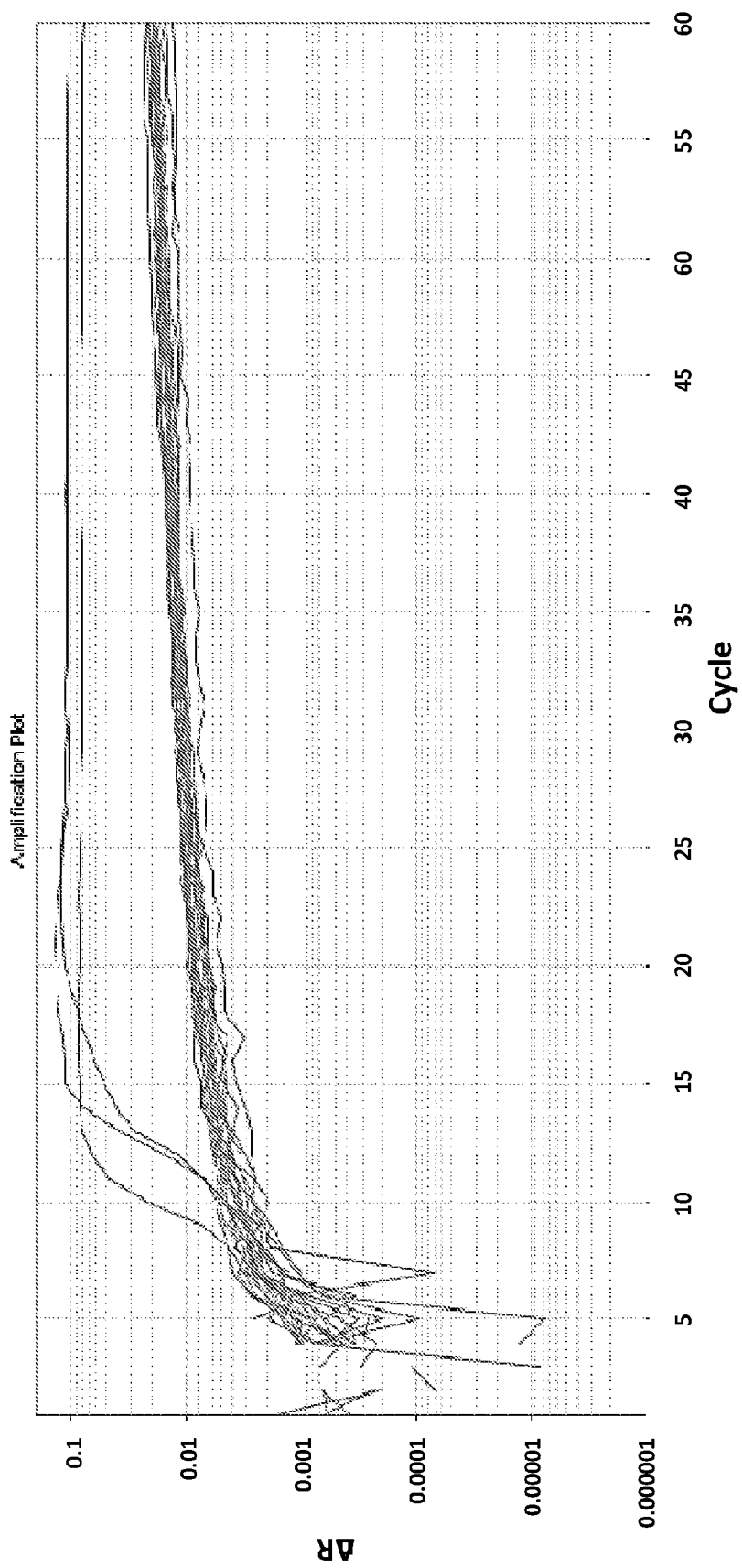
FIGS. 11A and 11B show the validation of CT PB1-FAM probe against APTIMA CT assay.
Figure 11B:
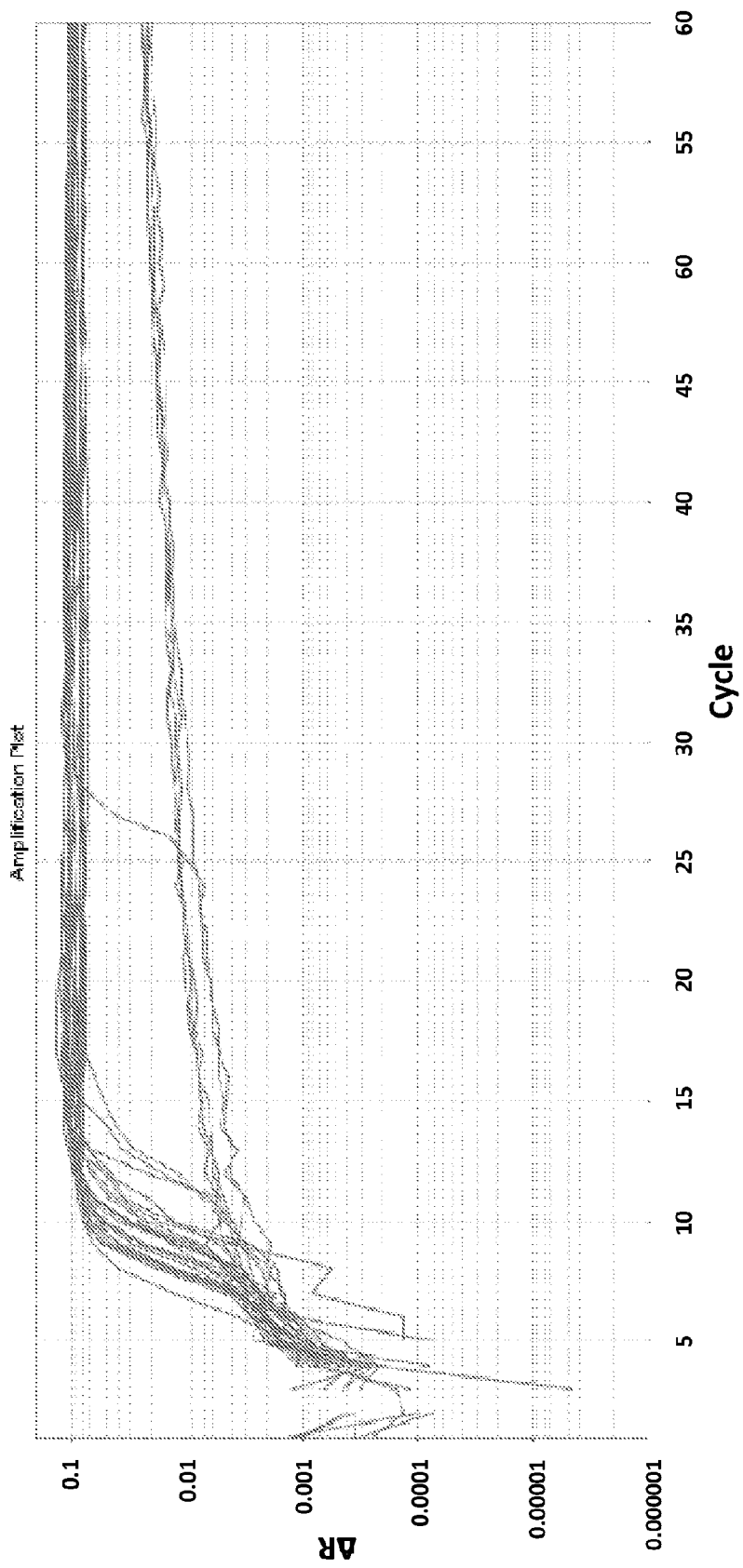

FIGS. 11A and 11B shows the validation of CT PB1-FAM probe against APTIMA CT assay. Fifty clinical samples confirmed to be positive (n=29) (FIG. 11A) or negative (n=21) (FIG. 11B) for CT were tested in V6.21p buffer with CT PB1-FAM probe. Out of 50 samples 24 tested negative (FIG. 11A) and 26 tested positive (FIG. 11B) for CT with CT PB1-FAM probe. There was 86% agreement between the Aptima and CT PB-FAM tests.

Example 11

Figure 12A:
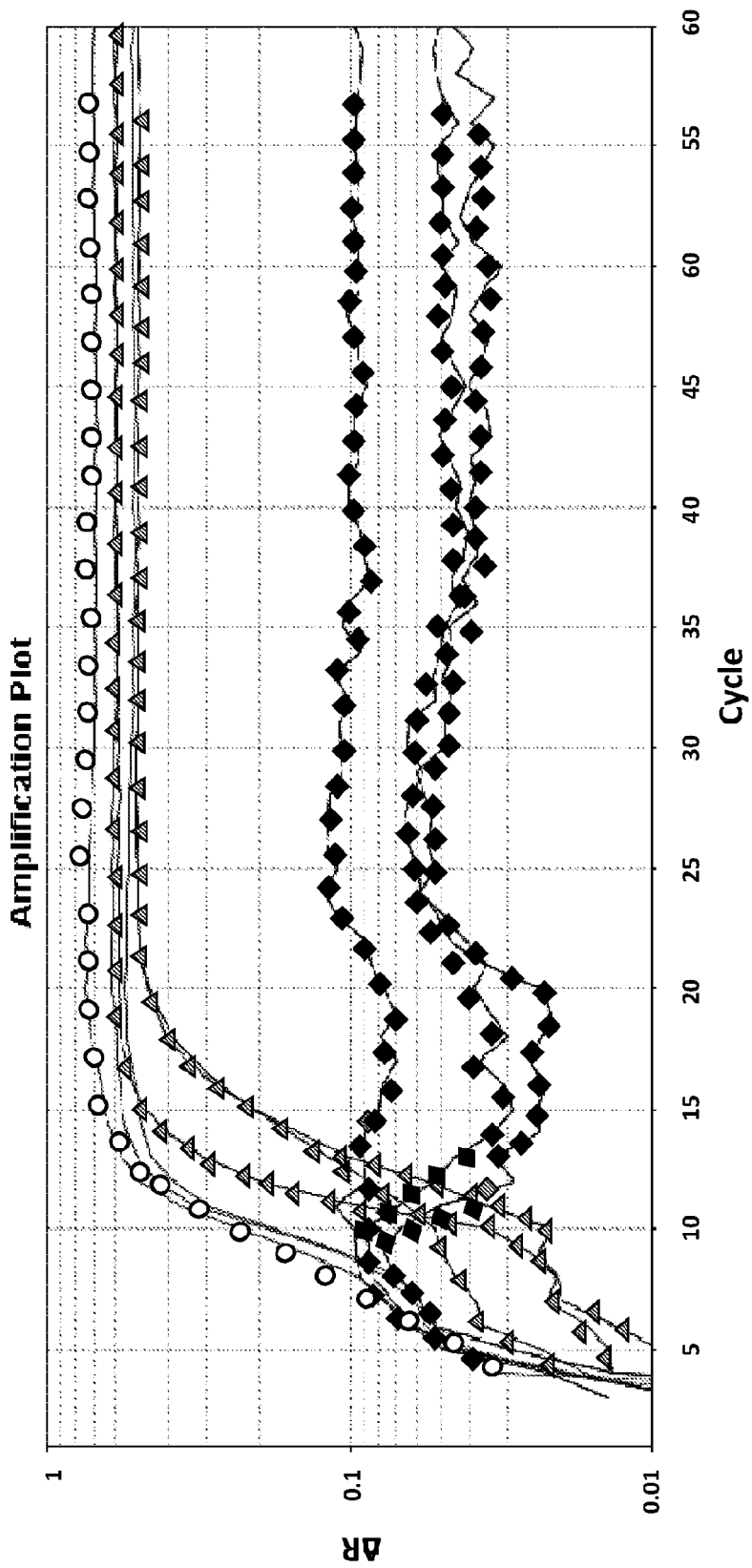
FIGS. 12A and 12B show the amplification plots generated in CT/GC multiplex with CT PB1-FAM+GC porA7-Alexa546 probes.
Figure 12B:
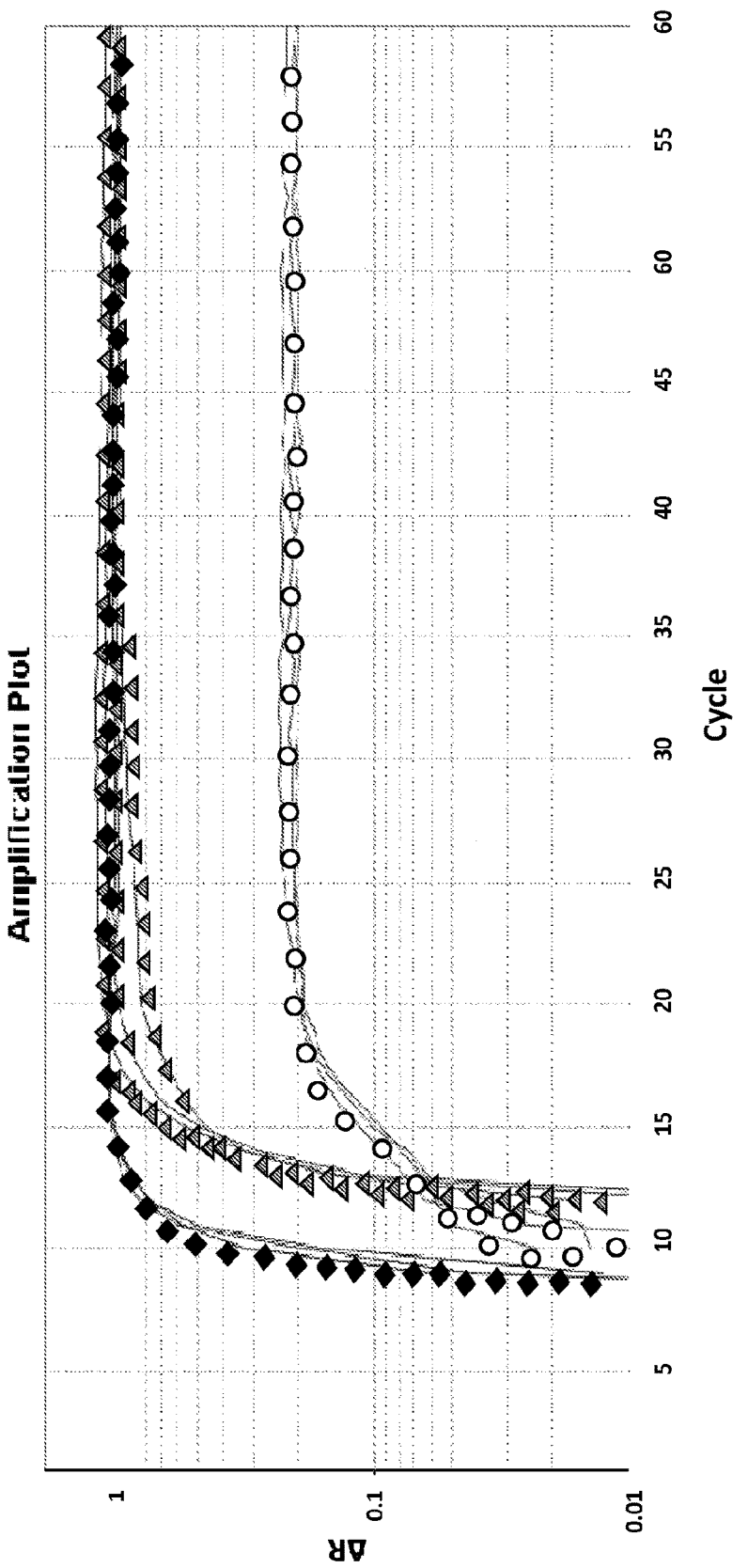

FIGS. 12A and 12B show the amplification plots generated in CT/GC multiplex with CT PB1-FAM+GC porA7-Alexa546 probes. CT and GC DNA was amplified in separate reactions or in conjugation in V6.21p buffer in the presence of CT PB1-FAM and GC porA7-Alexa546 probes. The readouts were taken in Cy3 (FIG. 12A) and FAM (FIG. 12B) channels. The experiment revealed that two DNA targets may be amplified and detected in a simultaneous reaction with FAM and Alexa546 labeled probes and that there was no cross reactivity between CT PB1 and GC porA7 primers and probes.

Example 12

Table 1 shows a comparison between V13 LAMP for CT and GC, CT/GC Aptima and CT/GC multiplex (CT PB1-FAM+GC porA7-Alexa546). DNA extracted from 136 clinical samples was tested with CT/GC Aptima multiplex, CT PB1 and GC porA7 primers in V6.21 buffer containing V13 or in a multiplex reaction in v6.21p buffer in the presence of CT PB1 and GC porA7 primers and CT PB1-FAM and GC porA7-Alexa546 probes. In a control experiment the samples were also tested in a simplex reaction with GC glnA7-joe probe. The table shows the agreement scores between the tests.

TABLE 1

Comparison between V13-based LAMP for CT and GC, CT/GC Aptima multiplex and CT/GC MAST multiplex (CT PB1-FAM + GC porA7-Alexa546). (Test on 136 clinical samples)

| Tests compared | Agreement score |
| --- | --- |
| CT LAMP vs CT PB1-FAM in multiplex | 92% |
| GC LAMP vs. GC porA7-Alexa546 in multiplex | 94% |
| CT in multiplex vs CT Aptima | 83% |
| GC in multiplex vs GC Aptima | 86% |

What is claimed is:

1. A method of detecting a target nucleic acid sequence in a sample, the method comprising:
   isothermally amplifying a target nucleic acid in the sample by loop-mediated isothermal amplification to provide an amplified nucleic acid, wherein the isothermal amplification incorporates a probe comprising an oligonucleotide sequence into the amplified nucleic acid, the oligonucleotide sequence being complementary to a region of a target nucleic acid sequence, wherein said oligonucleotide sequence has only one fluorophore label, which label is bound to an internal cytosine base that is not disposed in the first three bases from either the 5' or the 3' end, and wherein said probe comprising the oligonucleotide sequence does not have a 3' end terminator;
   measuring fluorescence of the incorporated fluorophore label in the amplified nucleic acid during the isothermal nucleic acid amplification; and
   detecting the presence of the target nucleic acid, wherein an increase in fluorescence of the amplified nucleic acid during the isothermal nucleic acid amplification indicates the presence of the target nucleic acid in the sample.

2. The method of claim 1, wherein the target nucleic acid is from a micro-organism, fungi, yeast or virus.

3. The method of claim 1, wherein the target nucleic acid is from *Chlamydia trachomatis* or *Neisseria gonorrhoeae*.

4. The method of claim 1, wherein the target nucleic acid is from human.

5. The method of claim 1, wherein the oligonucleotide probe sequence is a DNA sequence and the target nucleic acid sequence is a DNA sequence.

6. The method of claim 1, wherein the probe comprises the following sequence:

5'XnC*Xm3' wherein n is >3, m>3, X is nucleotide base; and * is fluorophore.

7. The method of claim 1, wherein the probe comprises one of the following sequences:
   SEQ ID NO: 2: TAAGATAAC[C-FAM]CCGCACGTG (CT PB1-FAM internal),
   SEQ ID NO: 4: GCGAACATA [C-ALEXA546] CAGCTATGATCAA (GC porA7-joe loopF), or
   SEQ ID NO: 5: ATGTTCA [C-JOE] CATGGCGGAG (GC glnA7-ALEXA546 loopB).

8. The method of claim 1, wherein the method utilizes more than one probe, each probe comprising a single fluorophore label.

9. The method of claim 8, wherein the single fluorophore label in each of the more than one probe is independently selected from the group consisting of: FAM, JOE, TET, HEX, TAMRA, ROX, ALEXA and ATTO.

10. The method as claimed in claim 9, wherein the single fluorophore label in each of the more than one probe is independently FAM, JOE or Alexa546.

11. The method of claim 1, wherein the single fluophore label is selected from the group consisting of: FAM, JOE, TET, HEX, TAMRA, ROX, ALEXA and ATTO.

12. The method as claimed in claim 11, wherein the single fluorophore label is FAM, JOE or Alexa546.

* * * * *

UNITED STATES PATENT AND TRADEMARK OFFICE
CERTIFICATE OF CORRECTION

| | |
|---|---|
| PATENT NO. | : 11,111,523 B2 |
| APPLICATION NO. | : 16/245190 |
| DATED | : September 7, 2021 |
| INVENTOR(S) | : Monika Iwona Suwara |

It is certified that error appears in the above-identified patent and that said Letters Patent is hereby corrected as shown below:

On the Title Page

On Page 2, Column 2, Item (56), Line 5, under Other Publications, delete "Moleulcar" and insert --Molecular--.

On Page 2, Column 2, Item (56), Line 10, under Other Publications, delete "Flurorescence" and insert --Fluorescence--.

In the Drawings

On Sheet 3 of 30, FIG. 2B, Line 10 (Approx.), in the x-axis labels, delete the first instance of "60" and insert --50--.

On Sheet 4 of 30, FIG. 2C, Line 10 (Approx.), in the x-axis labels, delete the first instance of "60" and insert --50--.

On Sheet 5 of 30, FIG. 2D, Line 10 (Approx.), in the x-axis labels, delete the first instance of "60" and insert --50--.

On Sheet 6 of 30, FIG. 2E, Line 10 (Approx.), in the x-axis labels, delete the first instance of "60" and insert --50--.

On Sheet 7 of 30, FIG. 2F, Line 10 (Approx.), in the x-axis labels, delete the first instance of "60" and insert --50--.

On Sheet 8 of 30, FIG. 3A, in the y-axis title, delete "(retropeRevitavireD )nrR" and insert --Derivative Reporter (-Rn')--.

On Sheet 9 of 30, FIG. 3B, in the y-axis title, delete ")nr(retropeRdezil a rnoN)" and insert --Normalized Reporter (Rn)--.

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 11,111,523 B2

On Sheet 10 of 30, FIG. 4A, in the y-axis title, delete ")nr(retropeRdezil a rnoN)" and insert --Normalized Reporter (Rn)--.

On Sheet 11 of 30, FIG. 4B, in the y-axis title, delete "(retropeRevitavireD )nrR" and insert --Derivative Reporter (-Rn')--.

On Sheet 12 of 30, FIG. 5A, in the y-axis title, delete "(retropeRevitavireD )nrR" and insert --Derivative Reporter (-Rn')--.

On Sheet 13 of 30, FIG. 5B, in the y-axis title, delete ")nr(retropeRdezil a rnoN)" and insert --Normalized Reporter (Rn)--.

On Sheet 14 of 30, FIG. 6A, in the y-axis title, delete "(retropeRevitavireD )nrR" and insert --Derivative Reporter (-Rn')--.

On Sheet 14 of 30, FIG 6A, in the y-axis labels, delete "20000.0" and insert --200000.0--.

On Sheet 15 of 30, FIG. 6B, in the y-axis title, delete "(retropeRevitavireD )nrR" and insert --Derivative Reporter (-Rn')--.

On Sheet 16 of 30, FIG. 6C, Line 15 (Approx.), in the x-axis labels, delete the first instance of "60" and insert --50--.

Figure 6D:
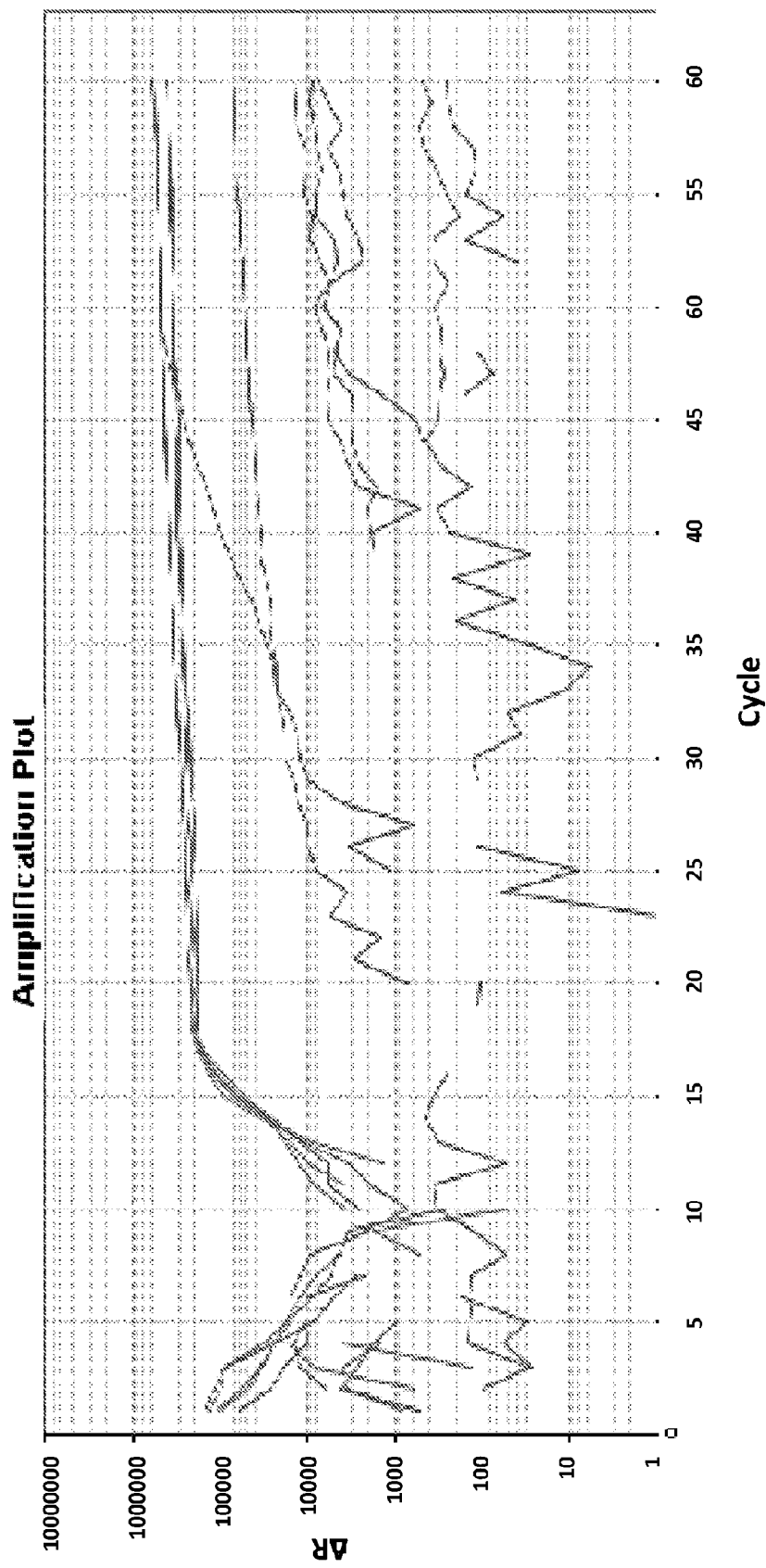

On Sheet 17 of 30, FIG. 6D, Line 10 (Approx.), in the x-axis labels, delete the first instance of "60" and insert --50--.

On Sheet 18 of 30, FIG. 7, in the y-axis title, delete "ecnecseroulF" and insert --Fluorescence--.

On Sheet 19 of 30, FIG. 8A, in the y-axis title, delete "ecnecseroulF" and insert --Fluorescence--.

On Sheet 20 of 30, FIG. 8B, in the y-axis title, delete "ecnecseroulF" and insert --Fluorescence--.

On Sheet 21 of 30, FIG. 9A, in the y-axis title, delete "ecnecseroulF" and insert --Fluorescence--.

On Sheet 22 of 30, FIG. 9B, Line 8 (Approx.), in the x-axis labels, delete the first instance of "60" and insert --50--.

On Sheet 23 of 30, FIG. 9C, in the y-axis title, delete "(retropeRevitavireD )nrR" and insert --Derivative Reporter (-Rn')--.

On Sheet 24 of 30, FIG. 10A, Line 9 (Approx.), in the x-axis labels, delete the first instance of "60" and insert --50--.

On Sheet 26 of 30, FIG 10C, please delete the label "CT probe, GC glnA7 primers GC DNA" and insert --CT probe, GC glnA7, primers, GC DNA--.

CERTIFICATE OF CORRECTION (continued)
U.S. Pat. No. 11,111,523 B2

On Sheet 26 of 30, FIG 10C, please delete the label "CT2 probe, GC porA7 primers GC DNA" and insert --CT2 probe, GC porA7, primers, GC DNA--.

On Sheet 27 of 30, FIG. 11A, Line 8 (Approx.), in the x-axis labels, delete the first instance of "60" and insert --50--.

On Sheet 28 of 30, FIG. 11B, Line 8 (Approx.), in the x-axis labels, delete the first instance of "60" and insert --50--.

On Sheet 29 of 30, FIG. 12A, Line 5 (Approx.), in the x-axis labels, delete the first instance of "60" and insert --50--.

On Sheet 30 of 30, FIG. 12B, Line 5 (Approx.), in the x-axis labels, delete the first instance of "60" and insert --50--.

In the Specification

In Column 2, Line 35, delete "fluororphore" and insert --fluorophore--.

In Column 3, Lines 49-50, delete "micro-organ-ism" and insert --microorganism--.

In Column 4, Line 32, delete "dNTPS" and insert --dNTPs--.

In Column 16, Line 54, delete "(100 fg GC DNA)" and insert --100 pg GC DNA))--.

In the Claims

In Column 36, Claim 11, Line 35 (Approx.), delete "fluophore" and insert --fluorophore--.